US006272377B1

(12) United States Patent
Sweeney et al.

(10) Patent No.: US 6,272,377 B1
(45) Date of Patent: Aug. 7, 2001

(54) CARDIAC RHYTHM MANAGEMENT SYSTEM WITH ARRHYTHMIA PREDICTION AND PREVENTION

(75) Inventors: Robert J. Sweeney, Woodbury; Bruce H. KenKnight, Maple Grove, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/411,345

(22) Filed: Oct. 1, 1999

(51) Int. Cl.[7] ................................................. A61B 5/0468
(52) U.S. Cl. ............................................................. 600/515
(58) Field of Search ..................................... 600/513, 518

(56) References Cited

U.S. PATENT DOCUMENTS

| | | | |
|---|---|---|---|
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,519,395 | 5/1985 | Hrushesky | 128/671 |
| 4,680,708 | 7/1987 | Ambos et al. | 364/417 |
| 4,732,157 | 3/1988 | Kaplan et al. | 128/696 |
| 4,754,753 | 7/1988 | King | 128/699 |
| 4,777,960 | 10/1988 | Berger et al. | 128/706 |
| 4,905,706 | 3/1990 | Duff et al. | 128/701 |
| 4,924,875 | 5/1990 | Chamoun | 128/696 |
| 4,930,075 | 5/1990 | Kortas | 364/413.06 |
| 4,960,129 | 10/1990 | dePaola et al. | 128/695 |
| 5,020,540 | 6/1991 | Cahmoun | 128/696 |
| 5,042,497 | 8/1991 | Shapland | 128/696 |
| 5,092,341 | 3/1992 | Kelen | 128/702 |
| 5,109,862 | 5/1992 | Kelen et al. | 128/702 |
| 5,113,869 | 5/1992 | Nappholz et al. | 128/696 |
| 5,148,812 | 9/1992 | Verrier et al. | 128/704 |
| 5,161,539 | 11/1992 | Evans et al. | 128/696 |
| 5,181,519 | 1/1993 | Bible | 128/704 |
| 5,188,116 | 2/1993 | Pommrehn et al. | 128/696 |
| 5,199,428 | 4/1993 | Obel et al. | 128/419 C |
| 5,203,326 | 4/1993 | Collins | 128/419 PG |
| 5,215,099 | 6/1993 | Haberl et al. | 128/702 |
| 5,217,021 | 6/1993 | Steinhaus et al. | 128/702 |
| 5,265,617 | 11/1993 | Verrier et al. | 128/704 |
| 5,277,189 | 1/1994 | Jacobs | 128/696 |
| 5,285,793 | 2/1994 | Slovut et al. | 128/706 |
| 5,318,037 | 6/1994 | Evans et al. | 128/696 |
| 5,318,592 | 6/1994 | Schaldach | 607/5 |
| 5,330,507 | 7/1994 | Schwartz | 607/14 |
| 5,377,687 | 1/1995 | Evans et al. | 128/700 |
| 5,411,531 | 5/1995 | Hill et al. | 607/14 |
| 5,419,338 | 5/1995 | Sarma et al. | 128/703 |
| 5,431,689 | 7/1995 | Weinberg et al. | 607/14 |
| 5,437,285 | 8/1995 | Verrier et al. | 128/702 |
| 5,507,784 | 4/1996 | Hill et al. | 607/14 |
| 5,509,425 | 4/1996 | Feng | 128/702 |
| 5,509,925 | 4/1996 | Adams et al. | 607/5 |

(List continued on next page.)

FOREIGN PATENT DOCUMENTS 0547733    6/1993    (EP)    ................................ A61N/1/36

Primary Examiner—William E. Kamm
(74) Attorney, Agent, or Firm—Schwegman, Lundberg, Woessner & Kluth, P.A.

(57) ABSTRACT

A cardiac rhythm management system predicts when an arrhythmia will occur and in one embodiment invokes a therapy to prevent or reduce the consequences of the arrhythmia. A cardiac arrhythmia trigger/marker is detected from a patient, and based on the trigger/marker, the system estimates a probability of a cardiac arrhythmia occurring during a predetermined future time interval. The system provides a list of triggers/markers, for which detection values are recurrently obtained at various predetermined time intervals. Based on detection values and conditional probabilities associated with the triggers/markers, a probability estimate of a future arrhythmia is computed. An arrhythmia prevention therapy is selected and activated based on the probability estimate of the future arrhythmia.

44 Claims, 9 Drawing Sheets

U.S. PATENT DOCUMENTS

| | | | |
|---|---|---|---|
| 5,534,015 | 7/1996 | Kroll et al. | 607/7 |
| 5,555,888 | 9/1996 | Brewer et al. | 128/702 |
| 5,555,889 | 9/1996 | Karagueuzian et al. | 128/705 |
| 5,560,367 | 10/1996 | Haardt et al. | 128/702 |
| 5,560,368 | 10/1996 | Berger | 128/703 |
| 5,560,370 | 10/1996 | Verrier et al. | 128/705 |
| 5,570,696 | 11/1996 | Arnold et al. | 128/707 |
| 5,578,061 | 11/1996 | Stroetmann et al. | 607/4 |
| 5,609,158 | 3/1997 | Cham | 128/705 |
| 5,645,069 | 7/1997 | Lee | 128/702 |
| 5,655,540 | 8/1997 | Seegobin | 128/702 |
| 5,658,318 | 8/1997 | Stroetmann et al. | 607/6 |
| 5,678,561 | 10/1997 | Karagueuzian et al. | 178/705 |
| 5,682,901 | 11/1997 | Kamen | 128/706 |
| 5,713,367 | 2/1998 | Arnold et al. | 128/704 |
| 5,730,142 | 3/1998 | Sun et al. | 128/705 |
| 5,749,900 | 5/1998 | Schroeppel et al. | 607/4 |
| 5,772,604 | 6/1998 | Langberg et al. | 600/518 |
| 5,778,881 | 7/1998 | Sun et al. | 128/696 |
| 5,782,888 | 7/1998 | Sun et al. | 607/27 |
| 5,785,702 | 7/1998 | Murphy-Chutorian et al. | 606/7 |
| 5,819,007 | 10/1998 | Elghazzawi | 395/51 |
| 5,868,680 | 2/1999 | Steiner et al. | 600/518 |
| 5,871,505 | 2/1999 | Adams et al. | 607/5 |
| 5,931,834 | 8/1999 | Murphy-Chutorian et al. | 606/7 |
| 6,064,906 | 5/2000 | Langberg et al. | 600/518 |
| 6,067,466 * | 5/2000 | Selker et al. | 600/513 |
| 6,115,627 * | 9/2000 | Street | 600/515 |

* cited by examiner

U = USE, X = DO NOT USE, --- = DO NOT CARE

| | #1 | #2 | #3 | #4 | #5 | #6 | #7 | #8 | ... | #M |
|---|---|---|---|---|---|---|---|---|---|---|
| TRIGGER/MARKER #1 | U | --- | --- | --- | --- | --- | --- | --- | ... | --- |
| TRIGGER/MARKER #2 | --- | U | --- | X | --- | U | --- | U | ... | X |
| TRIGGER/MARKER #3 | U | --- | X | U | --- | --- | U | --- | ... | --- |
| TRIGGER/MARKER #4 | --- | --- | U | --- | --- | U | --- | U | ... | U |
| TRIGGER/MARKER #5 | U | --- | --- | U | U | X | --- | --- | ... | --- |
| TRIGGER/MARKER #6 | --- | --- | --- | --- | --- | --- | --- | --- | ... | --- |
| ... | ... | ... | ... | ... | ... | ... | ... | ... | ... | ... |
| TRIGGER/MARKER #N | --- | --- | U | --- | --- | --- | U | --- | ... | --- |
| PREVENTIVE THERAPY | #1 | #2 | #3 | #4 | #5 | #6 | #7 | #8 | ... | #M |

CARDIAC RHYTHM MANAGEMENT SYSTEM WITH ARRHYTHMIA PREDICTION AND PREVENTION

TECHNICAL FIELD

This document relates generally to cardiac rhythm management systems and particularly, but not by way of limitation, to a system providing prediction of a future arrhythmia and preventive therapy for avoiding or mitigating the predicted arrhythmia.

BACKGROUND

The human heart normally maintains its own well-ordered intrinsic rhythm through generation of stimuli by pacemaker tissue that results in a wave of depolarization that spreads through specialized conducting tissue and then into and through the myocardium. The well-ordered propagation of electrical depolarizations through the heart causes coordinated contractions of the myocardium that results in the efficient pumping of blood. In a normally functioning heart, stimuli are generated under the influence of various physiological regulatory mechanisms to cause the heart to beat at a rate that maintains cardiac output at a level sufficient to meet the metabolic needs of the body. Abnormalities of excitable cardiac tissue, however, can lead to abnormalities of heart rhythm that are called arrhythmias. All arrhythmias stem from one of two causes: abnormalities of impulse generation or abnormalities of impulse propagation. Arrhythmias can cause the heart to beat too slowly (bradycardia, or a bradyarrhythmia) or too quickly (tachycardia, or a tachyarrhythmia), either of which may cause hemodynamic compromise or death.

Drug therapy is often effective in preventing the development of arrhythmias and in restoring normal heart rhythms once an arrhythmia has occurred. However, drug therapy is not always effective for treating particular arrhythmias, and drug therapy usually causes side-effects that may be intolerable in certain patients. For such patients, an alternative mode of treatment is needed. One such alternative mode of treatment includes the use of a cardiac rhythm management system incorporated into an implantable device that delivers therapy to the heart in the form of electrical stimuli. Such implantable devices include cardiac pacemakers that deliver timed sequences of low energy electrical stimuli, called pacing pulses, to the heart, via an intravascular leadwire or catheter (referred to as a lead) having one or more electrodes disposed in or about the heart. Heart contractions are initiated in response to such pacing pulses (referred to as capturing the heart). By properly timing the delivery of pacing pulses, the heart can be induced to contract in proper rhythm, greatly improving its efficiency as a pump. Pacemakers are often used to treat patients with bradycardia. Pacemakers are also capable of delivering paces to the heart in such a manner that the heart rate is slowed, a pacing mode referred to as anti-tachyarrhythmia pacing.

Cardiac rhythm management systems also include cardioverter/defibrillators (ICD's) that are capable of delivering higher energy electrical stimuli to the heart. ICD's are often used to treat patients with tachyarrhythmias, that is, hearts that beat too quickly. Tachyarrhythmias can cause diminished blood circulation because the cardiac cycle of systole (contraction) and diastole (filling) can be shortened to such an extent that insufficient blood fills the ventricles during diastole. Besides the potential for such hemodynamic embarrassment, tachyarrhythmias can also degrade into even more serious arrhythmias such as fibrillation where electrical activity spreads through the myocardium in a disorganized fashion so that effective contraction does not occur. For example, in a particular type of tachyarrhythmia, referred to as ventricular fibrillation, the heart pumps little or no blood to the body so that death occurs within minutes. A defibrillator delivers a high energy electrical stimulus or shock to the heart to depolarize all of the myocardium and render it refractory in order to terminate arrhythmia, allowing the heart to reestablish a normal rhythm for the efficient pumping of blood. In addition to ICD's and pacemakers, cardiac rhythm management systems also include pacemaker/ICD's that combine the functions of pacemakers and ICD's, drug delivery devices, and any other implantable or external systems or devices for diagnosing, monitoring, or treating cardiac arrhythmias.

Cardiac rhythm management systems incorporated into ICD's allow tachyarrhythmias to be automatically detected and treated in a matter of seconds. Defibrillators are usually effective at treating tachyarrhythmias and preventing death, but such devices are not 100% effective at treating all tachyarrhythmias in all patients. As a result, some patients may still die even if the defibrillator delivers appropriate therapy. Also, some patients have frequent tachyarrhythmias, triggering frequent therapeutic shocks. This reduces the usable life of the implanted battery-powered device and increases the risk of therapy-induced complications. Furthermore, even if the device successfully treats the tachyarrhythmia, the patient may lose consciousness during the arrhythmia which can result in related serious or even fatal injuries (e.g., falling, drowning while bathing, car accident while driving, etc.). Thus, there is a need for a cardiac rhythm management system that predicts when an arrhythmia will occur and invokes a therapy to prevent or reduce the consequences of the arrhythmia.

SUMMARY

The present invention relates to a system and method for predicting cardiac arrhythmias. In a particular embodiment, the system and method are implemented in an implantable cardiac device having one or more sensing channels for detecting conditioning events (e.g., marker/trigger events as defined below) and the capability of delivering some type of preventive arrhythmia therapy when conditions warrant it.

In accordance with the invention, an arrhythmia is predicted by: 1) detecting a conditioning event statistically associated with the occurrence of an arrhythmia in a patient's heart; 2) computing a conditional arrhythmia probability for the conditioning event from past observations of instances in which the conditioning event occurs alone or together with an arrhythmia within a specified time period; 3) computing an estimated arrhythmia probability based upon the detected occurrence of the conditioning event; and 4) predicting the occurrence of an arrhythmia within a specified prediction time period if the estimated arrhythmia probability exceeds a specified threshold value.

Conditioning events may be broadly classified into markers and triggers. A marker event corresponds to detected a physiological state that is statistically associated with occurrence of cardiac arrhythmias, but the causal relationship between the marker and the arrhythmia is not known. A conditioning event is regarded as a trigger, on the other hand, if the event is thought to increase the risk of an arrhythmia occurring via a depolarization that serves as a source for the arrhythmia. Conditioning events may be detected on a beat-to-beat basis or over a longer time frame. Examples of conditioning events include a detected specific morphology of a waveform representing the electrical activity of the heart, a specific pattern of activation times of different areas of the heart as sensed by a plurality of electrodes, a specific sequence pattern of heartbeats with respect to time, a value of a measured physiological variable such as heart rate or blood pressure, or a statistic based upon a history of occurrences of conditioning events.

In one embodiment, the conditional arrhythmia probability is calculated as a ratio of the number of observed instances in which the conditioning event is followed by an arrhythmia within a specified basic time period, to the total number of observed instances of the conditioning event. In that case, the estimated arrhythmia probability for an arrhythmia to occur within the specified basic time period after detection of the conditioning event is simply the calculated conditional arrhythmia probability.

In another embodiment, the conditional arrhythmia probability CP is calculated by the expression:

$$CP=1-e^{-RT}$$

which assumes a Poisson probability distribution, where T is a measure of the specified prediction time period, and R is an estimate of the rate at which arrhythmias occur while the conditioning event is present. The rate R is a ratio of: 1) the number of instances in which the conditioning event is followed by an arrhythmia within a specified basic time period, to 2) the length of the basic time period multiplied by the total number of basic time periods in which the conditioning event is observed. The estimated arrhythmia probability for an arrhythmia to occur within the time T after detection of the conditioning event is again the conditional arrhythmia probability. Calculating the conditional arrhythmia probability in this manner allows the prediction time period T to differ from the length of the basic time period used to derive the conditional arrhythmia probability.

In another embodiment, rather than basing the estimated arrhythmia probability upon the detection of a conditioning event, a rate at which the conditioning event occurs is detected over some period of time. The estimated arrhythmia probability is then calculated as the product of an estimated probability that a conditioning event will occur times the probability of an arrhythmia occurring within specified time period given the occurrence of the conditioning event (i.e. the conditional arrhythmia probability). Thus:

$$\text{estimated arrhythmia probability}=(1-e^{-RT})(1-e^{-CT})$$

where T is a measure of the specified prediction time period, R is an estimate of the rate at which arrhythmias occur while the conditioning event is present, and C is an estimate of the rate at which the conditioning event occurs.

Another way of deriving a conditional arrhythmia probability, especially for trigger-types of conditioning events (although it can be used with any type of conditioning event), is to designate a particular detected trigger event as being responsible for causing a detected arrhythmia. Such culpability may be assigned based, e.g., upon the proximity in time between the trigger event and the onset of the arrhythmia, the magnitude of the detected trigger, or the frequency of occurrence of the trigger event within a specific time period prior to the onset of the arrhythmia. A conditional arrhythmia probability CP for that trigger event can then be calculated as a ratio of the number of instances in which the trigger event was deemed culpable for causing an arrhythmia, to the total number of occurrences of the trigger event. Also, as above, rather than basing the estimated arrhythmia probability upon the detection of the trigger event, a rate at which the trigger event occurs can be detected over some period of time. The estimated arrhythmia probability is then calculated as the product of an estimated probability that a trigger event will occur times the probability CP of an arrhythmia occurring within a specified time period T given the occurrence of the trigger event. Thus:

$$\text{estimated arrhythmia probability}=CP\times(1-e^{-CT})$$

In a preferred embodiment, the prediction of arrhythmias is based upon a plurality of the same or different detected conditioning events. A composite estimated arrhythmia probability is then computed as a combination of the estimated arrhythmia probabilities derived for each separately detected conditioning event. The separately detected conditioning events may be separate occurrences of the same or different conditioning events. As before, the composite arrhythmia probability is compared with a threshold value in order to predict the occurrence of an arrhythmia. In one embodiment, the composite arrhythmia probability is calculated by adding the individual estimated arrhythmia probabilities derived for each detected conditioning event, which thus assumes each individual arrhythmia probability to correspond to an independent event. In other embodiments, specific combinations of detected conditioning events are mapped in a non-linear fashion to estimated arrhythmia probabilities that can be added or otherwise combined with other estimated arrhythmia probabilities to give a composite value. In still other embodiments, the estimated arrhythmia probability is computed from a combination of conditional arrhythmia probabilities derived using different basic time periods but for the same prediction time period.

The past observations of the occurrences of conditioning events and arrhythmias from which the conditional arrhythmia probabilities are derived can be taken from either population data or from data collected in real-time from a particular patient. In a preferred embodiment, the conditional arrhythmia probabilities are based initially upon past observations of the occurrences of events and arrhythmias taken from population data, and each probability is subsequently updated from a previous value to a present value with observations taken in real-time from a particular patient. In one embodiment, a conditional arrhythmia probability is updated only if the present value differs by a predetermined amount from the previous value. In another embodiment, the amount by which the present value differs from the previous value is tested for statistical significance before a conditional arrhythmia probability is updated. In another embodiment, the previous value of the conditional arrhythmia probability is incremented or decremented by a specific amount after a prediction time period in accordance with whether the arrhythmia occurred or not, respectively.

In still another embodiment, the statistical association between the conditioning event and the occurrence of an arrhythmia is periodically reevaluated using the most recent patient-specific data. If the statistical association (e.g., as a calculated from a chi-square test) is found to be below a specified value, the use of that conditional arrhythmia probability in deriving a composite estimated arrhythmia probability is discontinued.

As aforesaid, one embodiment of the invention involves delivering preventive arrhythmia therapy if the estimated probability of an arrhythmia occurring within a specified time period (i.e., the composite estimated arrhythmia probability) exceeds a threshold value so that an arrhythmia can be predicted with some degree of certainty. Examples of such therapies capable of being delivered by an implantable device include the delivery of pharmacologic agents, pacing the heart in a particular mode, delivery of cardioversion/ defibrillation shocks to the heart, or neural stimulation (e.g., stimulation of either the sympathetic or parasympathetic branches of the autonomic nervous system). Another type of therapy capable of being delivered by an implantable device in accordance with the invention (interpreting the term "therapy" in a broad sense) is issuance of a warning signal that an arrhythmia has been predicted, which warning signal may take the form of a audible signal, a radio-transmitted signal, or any other type of signal that would alert the patient or physician to the possibility of an impending arrhythmia. Such a warning signal would allow the patient to take precautionary measures and/or allow a treating physician to take other therapeutic steps if deemed appropriate. In accordance with the invention, the selection of a particular therapy to be delivered or not is based upon ascertaining a physiologic state of the patient and deciding whether or not a particular available modality of therapy is appropriate for delivery to the patient in that physiologic state.

The modality selection process in one embodiment takes the form of a matrix mapping of a state vector representing a specific physiologic state (as determined by, e.g., the particular conditioning events used to make the arrhythmia prediction, the prediction time period for the estimated arrhythmia probability, the presence or not of specific conditioning events within a specified prior time period, or the magnitude and/or presence other detected and/or calculated variables) to a specific therapy or therapies considered most appropriate for preventing an arrhythmia in that instance (i.e., a point in "therapy space"). The matrix mapping is performed using a therapy matrix containing information relating to whether or not (and/or to what extent) a particular therapy modality is expected to be effective for a given physiologic state. The elements of the therapy matrix may thus constitute variables representing the appropriateness of a particular therapy modality given the presence of a specific element in the physiological state vector.

In one particular embodiment, a prediction scheduler makes separate predictions for each time period in which an arrhythmia may or may not be predicted to occur (i.e., the prediction time period) and then makes a therapy decision using a therapy matrix specific for that prediction time period. In this manner, a therapy decision for a given therapy modality may be made with respect to the time period appropriate for that modality. For example, some therapy modalities can be expected to be effective in a short time period and are thus suitable for preventing an arrhythmia with a short prediction time period, while others would not be expected to be effective until after a longer time interval and therefore would only be suitable if the prediction time period were commensurate. In another embodiment, therapy decisions and predictions are made at time intervals without regard to the arrhythmia prediction periods, and the therapy matrix takes into account the prediction time period for the estimated arrhythmia probability. For example, the prediction time period may be incorporated into the physiologic state vector, and the therapy matrix then contains information related to the appropriateness of each available therapy modality for a given prediction time period.

Rather than estimating a probability for the occurrence of any arrhythmia, separate estimated arrhythmia probabilities can be computed for different types of arrhythmias in accordance with the invention. By computing such separate probabilities, a more informed decision as to what mode of therapeutic intervention to employ may be made. The most beneficial set of separate estimated arrhythmia probabilities for any particular patient be expected to vary. Accordingly, selection of the arrhythmia types for which separate estimated arrhythmia probabilities are computed can be done dynamically by tabulating the number of detected occurrences of each specific type of arrhythmia and computing separate estimated arrhythmia probabilities for those arrhythmia types occurring most frequently in the patient. Separate estimated arrhythmia probabilities can also be computed for different types of trigger events. Such trigger events can be expected to be patient-specific, and the particular mix of trigger events for which separate arrhythmia probabilities are calculated can be selected dynamically as described above.

BRIEF DESCRIPTION OF THE DRAWINGS

In the drawings, like numerals describe substantially similar components throughout the several views. Like numerals having different letter suffixes represent different instances of substantially similar components.

FIG. 8 is a diagram illustrating generally one embodiment of a translation matrix.

DETAILED DESCRIPTION

Figure 1:
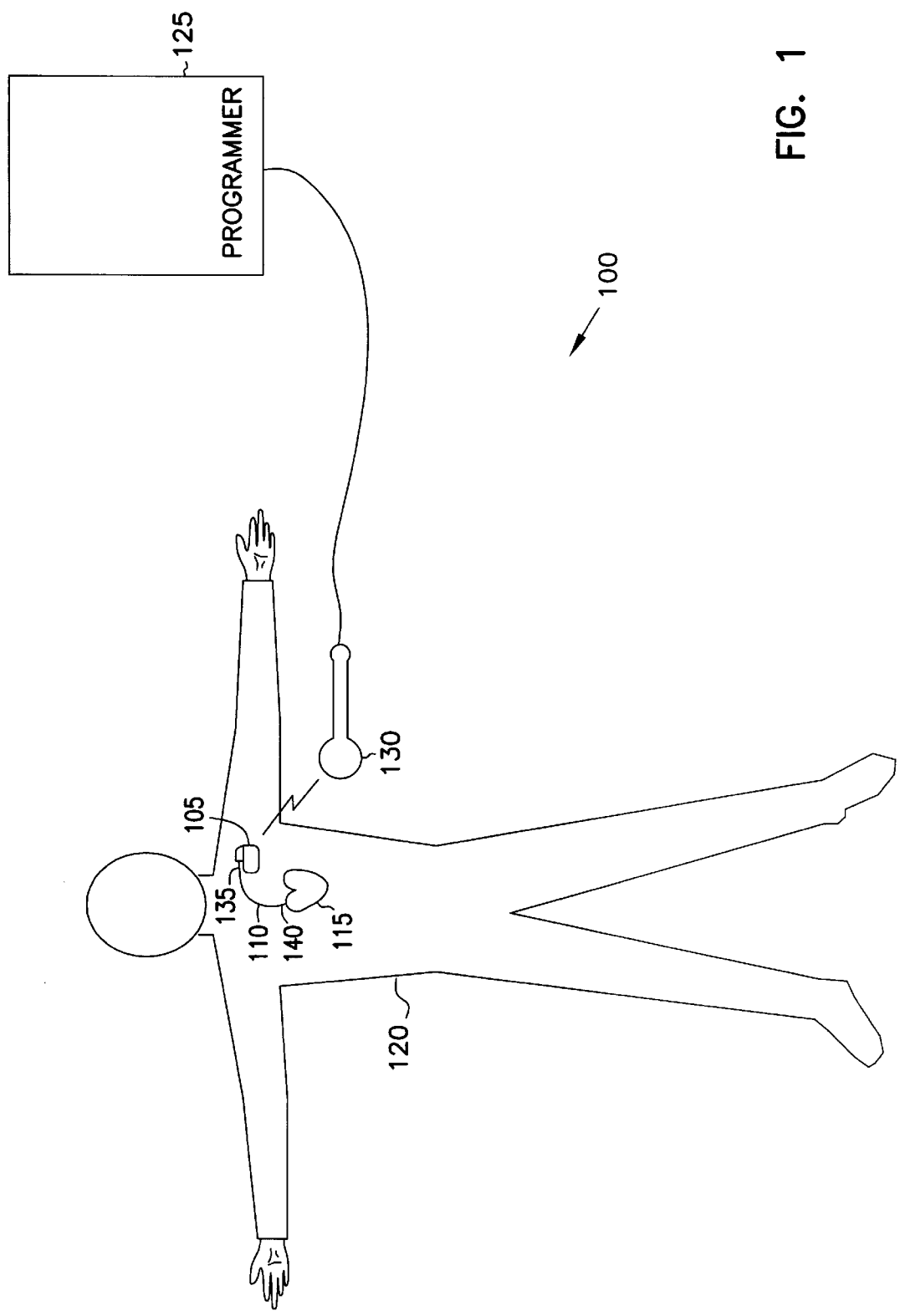
FIG. 1 is a schematic drawing illustrating generally one embodiment of portions of a cardiac rhythm management system and an environment in which it is used.

This invention relates to a cardiac rhythm management system that predicts when an arrhythmia will occur based upon the detection of conditioning events found to be statistically associated with the occurrences of arrhythmias. A further embodiment uses the prediction to invoke a therapy to prevent or reduce the consequences of the arrhythmia. The present system may incorporate several features including: (1) distinguishing a degree of risk for occurrence of a future arrhythmia, (2) making predictions that apply to a well defined future time interval, (3) basing predictions on direct observations of arrhythmic triggers/ markers (i.e., conditioning events) using conditional probabilities that these arrhythmias will occur given the past and present occurrences of the arrhythmias and the triggers/ markers, (4) assessing a confidence in the accuracy of the prediction, (5) adapting its prediction and prevention capabilities to the individual patient, (6) assessing the expected effect of one or multiple preventive therapies in order to determine if the likelihood for future arrhythmias is increased or decreased by the proposed preventive therapies, (7) selecting a therapy based on this assessment of its expected effect, and (8) determining whether the selected preventive therapy combination should be invoked based on the magnitude, timing and confidence in the arrhythmia prediction and of the expected effect of the selected therapy. In one embodiment, the system also includes an external programmer device that can control, load and retrieve information from the implanted cardiac rhythm management device, and which can process and display information obtained from the implanted device. The present system provides techniques for predicting and preventing future cardiac arrhythmias, and such techniques can be used in combination with pacing, defibrillation, and other therapy techniques for treating presently existing cardiac arrhythmias.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present methods and apparatus will be described in applications involving implantable medical devices including, but not limited to, implantable cardiac rhythm management systems such as pacemakers, cardioverter/defibrillators, pacemaker/defibrillators, and biventricular or other multi-site coordination devices. However, it is understood that the present methods and apparatus may also be employed in unimplanted devices of the same sort, as well as in external monitors, programmers and recorders.

Herein, the term "prediction" is used to mean a probability statement regarding whether or not an arrhythmia will occur at a future time. The term "trigger" refers to one or more cardiac events, such as depolarizations or other intrinsic heart activity signals, that may trigger an arrhythmia. Examples of such triggers include, by way of example, but not by way of limitation: sinus beats, premature sinus beats, beats following long sinus pauses; long-short beat sequences, R on T-wave beats, ectopic ventricular beats, and premature ventricular beats. The term "marker" refers to one or more quantities associated with at least one abnormal physiologic state (e.g., the occurrence of an arrhythmia) in which the quantity is obtainable from one or more electrophysiologic signals, or from one or more signals from one or more other sensors. Examples of such markers include, by way of example, but not by way of limitation: ST elevations, heart rate, increased or decreased heart rate, abnormal heart rate variability, late-potentials, or abnormal autonomic activity.

Overview

FIG. 1 is a schematic drawing illustrating generally, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. In one embodiment, external programmer 125 includes a visual or other display for providing information to a user regarding operation of implanted device 105. Catheter lead 110 includes a proximal end 135, which is coupled to device 105, and a distal end 140, which is coupled to one or more portions of heart 115.

Figure 2:
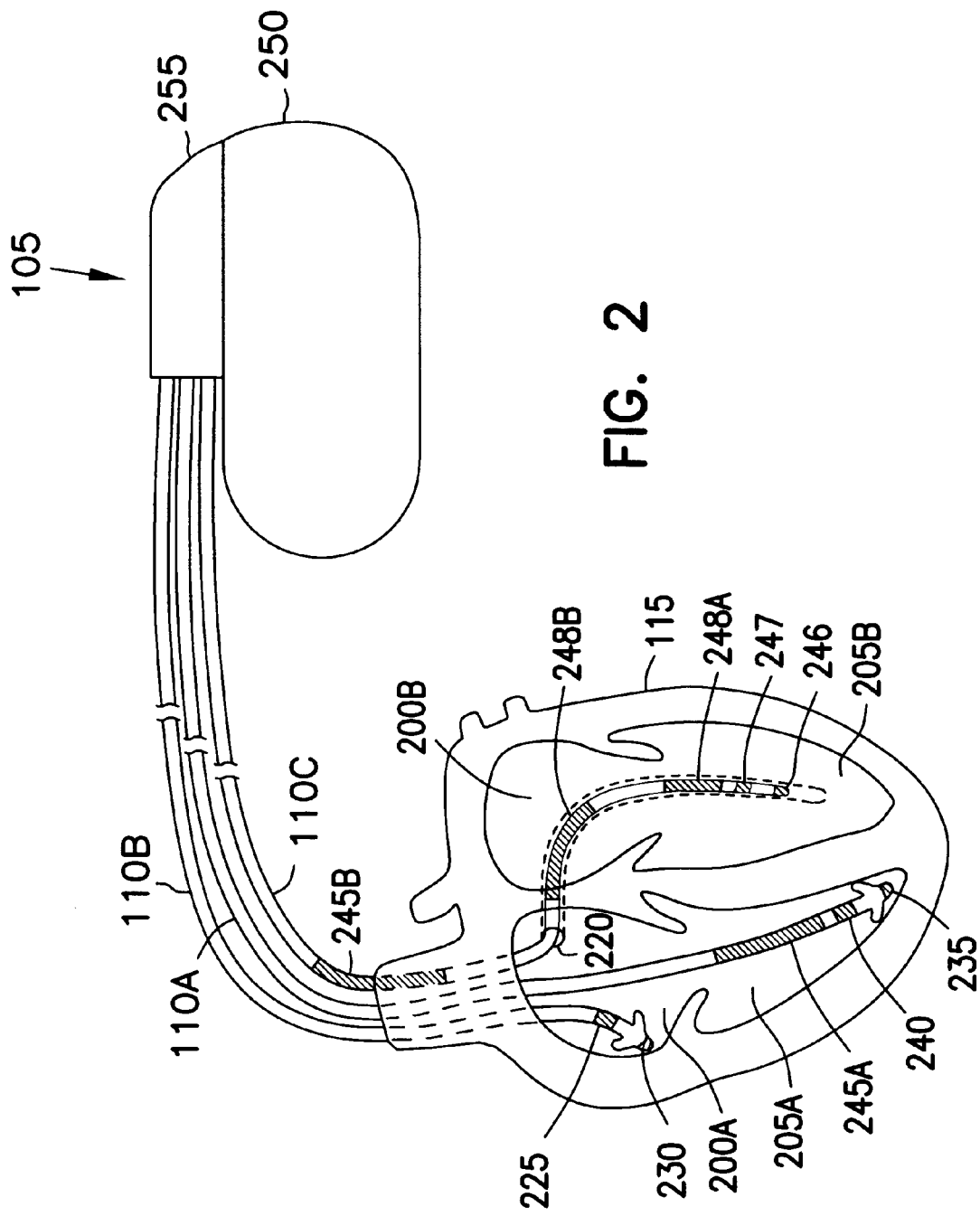
FIG. 2 is a schematic drawing illustrating generally one embodiment of a cardiac rhythm management device coupled by leads to a heart.

FIG. 2 is a schematic drawing illustrating generally, by way of example, but not by way of limitation, one embodiment of device 105 coupled by leads 110A–C to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a right ventricular lead 110B includes one or more electrodes, such as tip electrode 235 and ring electrode 240, for sensing signals and/or delivering pacing therapy. Lead 110B optionally also includes additional electrodes, such as coil electrodes 245A–B for delivering right atrial and/or right ventricular cardioversion/defibrillation and/or pacing therapy to heart 115. In one embodiment, system 100 also includes a left ventricular lead 110C, which provides one or more electrodes such as tip electrode 246 and ring electrode 247, for sensing signals and/or delivering pacing therapy. Lead 110C optionally also includes one or more additional electrodes, such as coil electrodes 248A–B for delivering left atrial and/or left ventricular cardioversion/defibrillation and/or pacing therapy to heart 115.

In FIG. 2, device 105 includes components that are enclosed in a hermetically-sealed enclosure, such as can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help direct electrical currents produced by device 105. For example, an electrode on header 255 may be used to stimulate local muscle to provide an alert/warning to the patient. In another example, an additional lead is used to provide electrodes associated with nerves or nerve ganglia, such as the vagus nerve, left or right stellate ganglion, carotid sinus nerve, or the fat pad over the atrioventricular node. The present method and apparatus will work in a variety of configurations and with a variety of electrical contacts or electrodes.

Figure 3:
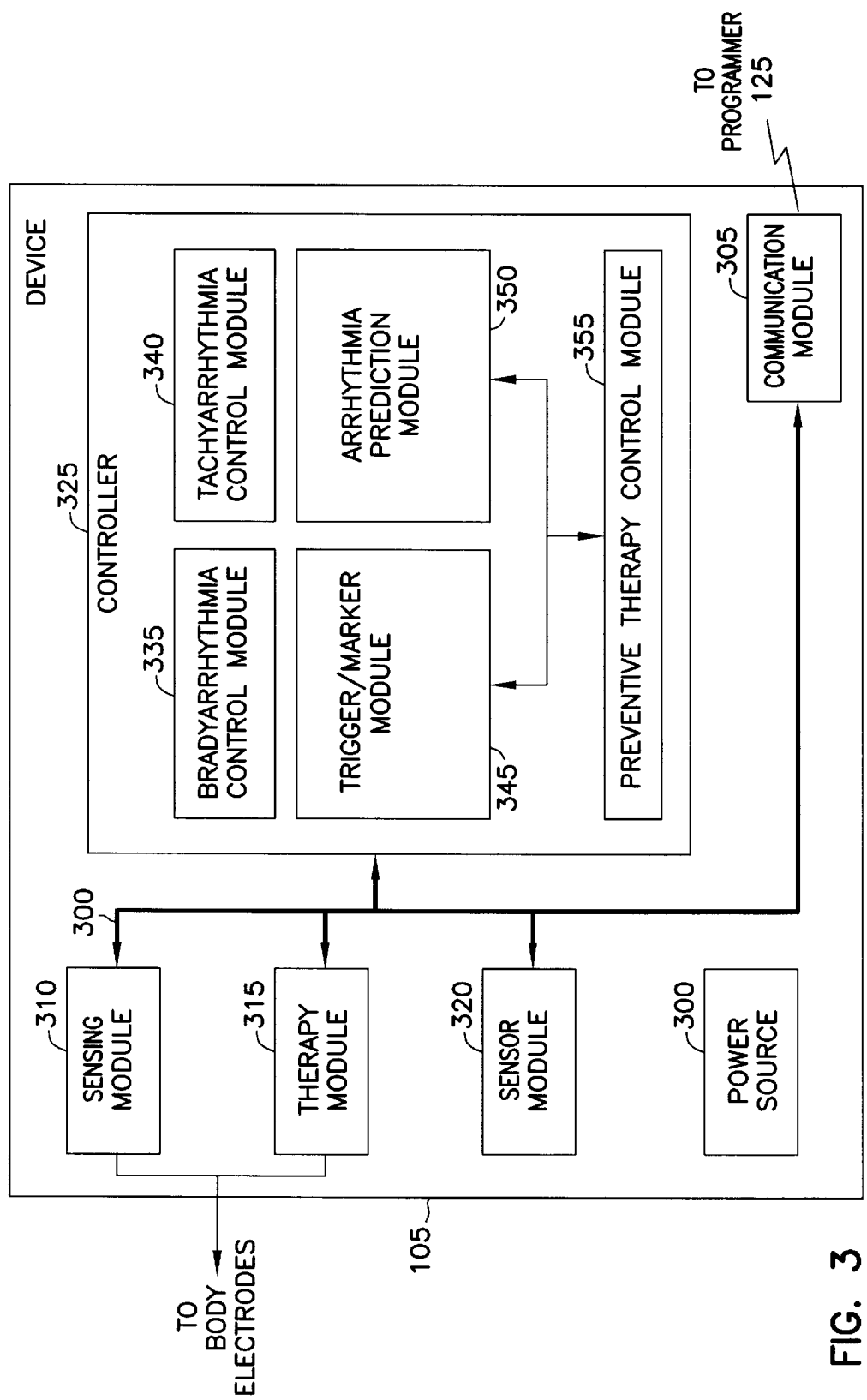
FIG. 3 is a schematic diagram illustrating generally one embodiment of portions of a cardiac rhythm management device, which is coupled to a heart and/or other portions of the patient's body.

FIG. 3 is a schematic diagram illustrating generally, by way of example, but not by way of limitation, one embodiment of portions of device 105, which is coupled to heart 115 and/or other portions of the patient's body. FIG. 3 illustrates one conceptualization of various modules, which are implemented either in hardware or as one or more sequences of steps carried out on a microprocessor or other controller. Such modules are illustrated separately for conceptual clarity; it is understood that the various modules of FIG. 3 need not be separately embodied, but may be combined and/or otherwise implemented, such as in software/firmware. In FIG. 3, device 105 includes, among other things, a power source 300, such as a battery. A communication module 305 includes a telemetry or other circuit by which implantable device 105 communicates with external programmer 125. A sensing module 310 senses intrinsic heart activity signals from one or more electrodes associated with heart 115. In one embodiment, sensing module 310 also senses other electrophysiological signals. A therapy module 315 provides therapy for treatment of present arrhythmias and prevention of future arrhythmias. In one embodiment, such therapy is provided at electrodes associated with heart 115 or portions of the nervous system such as, for example but without limitation, to sense other electrophysiological signals such as activity from sympathetic or parasympathetic members of the autonomic nervous system, or to sense blood temperature or blood flow. In various embodiments such therapy includes, among other things, pacing pulses, anti-tachyarrhythmia pacing (ATP), defibrillation shocks, etc.

In FIG. 3, sensing module 320 includes, among other things, one or more sensors, such as an accelerometer, acoustic sensor, respiration and/or stroke volume sensor (e.g., using transthoracic impedance), time and/or date of detected arrhythmia(s), cardiac displacement or blood vessel dimensions (e.g., using ultrasonic transit time measurements), or blood electrolyte levels (e.g., using ion-selective membranes). Sensing module 320 also includes interface circuits that receive control signals and preprocess the sensor signal(s). Device 105 also includes a control circuit, such as a microprocessor or other controller 325, which communicates with various peripheral circuits via one or more nodes, such as bus 330. Controller 325 includes various functional blocks, one conceptualization of which is illustrated in FIG. 3.

In one embodiment, controller 325 includes a bradyarrhythmia control module 335 that detects bradyarrhythmias based at least in part on one or more signals obtained from sensing module 310. Bradyarrhythmia control module 335 also provides one or more physiologically appropriate anti-bradyarrhythmia therapies to treat presently existing bradyarrhythmias. A tachyarrhythmia control module 340 detects tachyarrhythmias based at least in part on one or more signals obtained from sensing module 310. Tachyarrhythmia control module 340 also provides one or more physiologically appropriate anti-tachyarrhythmia therapies to treat presently existing tachyarrhythmias.

For predicting and preventing arrhythmias, controller 325 also includes trigger/marker module 345, arrhythmia prediction module 350, and preventive therapy control module 355. Trigger/marker module 345 detects one or more triggers and/or markers based at least in part on signals received from sensing module 310 and/or sensing module 320. Arrhythmia prediction module 450 predicts the likelihood of future arrhythmias using probability calculations based on trigger/marker information received from trigger/marker module 345. Preventive therapy control module 355 selects the most appropriate therapy (or combination of therapies) for preventing the future arrhythmia from a set of available preventive therapies. Preventive therapy control module 355 also triggers the delivery of such therapy after determining if the probability of arrhythmia, computed by arrhythmia prediction module 350, and the expected outcome of the selected therapy warrants administration of the therapy by therapy module 315. Thus, device 105 predicts and prevents future arrhythmias, as described more particularly below. In one embodiment, the prediction and prevention of future arrhythmias is deactivated if one or more present arrhythmias (e.g., ventricular tachyarrhythmia (VT) or ventricular fibrillation (VF)) are present and are being treated by techniques, known to one skilled in the art, using tachyarrhythmia control module 340 and/or bradyarrhythmia control module 335.

Example of Detecting Arrhythmogenic Trigger(s)/Marker(s)

Figure 4A:
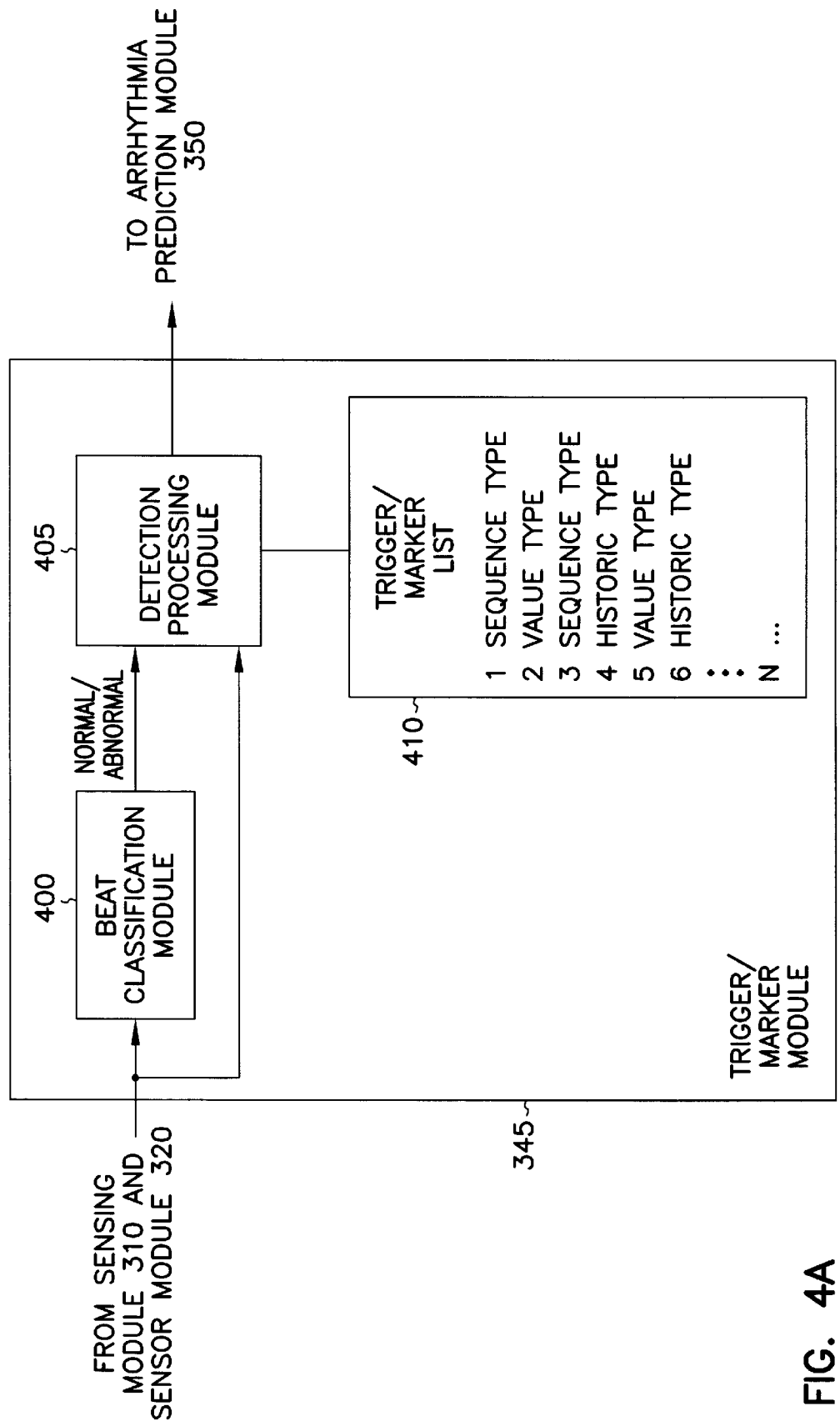
FIG. 4A is a block diagram illustrating generally one conceptual embodiment of portions of a trigger/marker module.

FIG. 4A is a block diagram illustrating generally, by way of example, but not by way of limitation, one conceptual embodiment of portions of trigger/marker module 345. In this embodiment, trigger/marker module 345 includes beat classification module 400, detection processing module 405, and a trigger/marker data bank such as trigger/marker list 410. Trigger/marker module 345 recurrently examines signals from sensing module 310 and/or sensing module 320 and detects the presence, timing, and (if appropriate) magnitude of triggers/markers. These detections, timings, and magnitudes are output to detection processing module 405 either for each heartbeat, or corresponding to a time period encompassing multiple heartbeats.

Beat classification module 400 examines signals from variously located electrodes. On a beat-to-beat basis, beat classification module 400 distinguishes between depolarization events that spread over the heart normally from those that spread out over the heart abnormally. Normal beats refer to those beats that are most prevalent and physiologically sound in the patient, even though the patient's most prevalent beat type might not be considered normal when compared to the propagation of a depolarization in a healthy heart. In one embodiment, sensing module 310 provides and beat classification module analyzes signals from: a right atrial sensing electrode (RA), a right ventricular sensing electrode (RV), a left ventricular (LV) sensing electrode, a right sided morphology (RM) signal between defibrillation electrodes in the right ventricular and superior vena cava and/or the metallic shell of the device, a left sided morphology (LM) signal between a left ventricular electrode and one or more of the other electrodes. Several example methods of operating beat classification module 400 to classify heart beats as normal or abnormal are described below by way of example, but not by way of limitation.

Figure 4B:
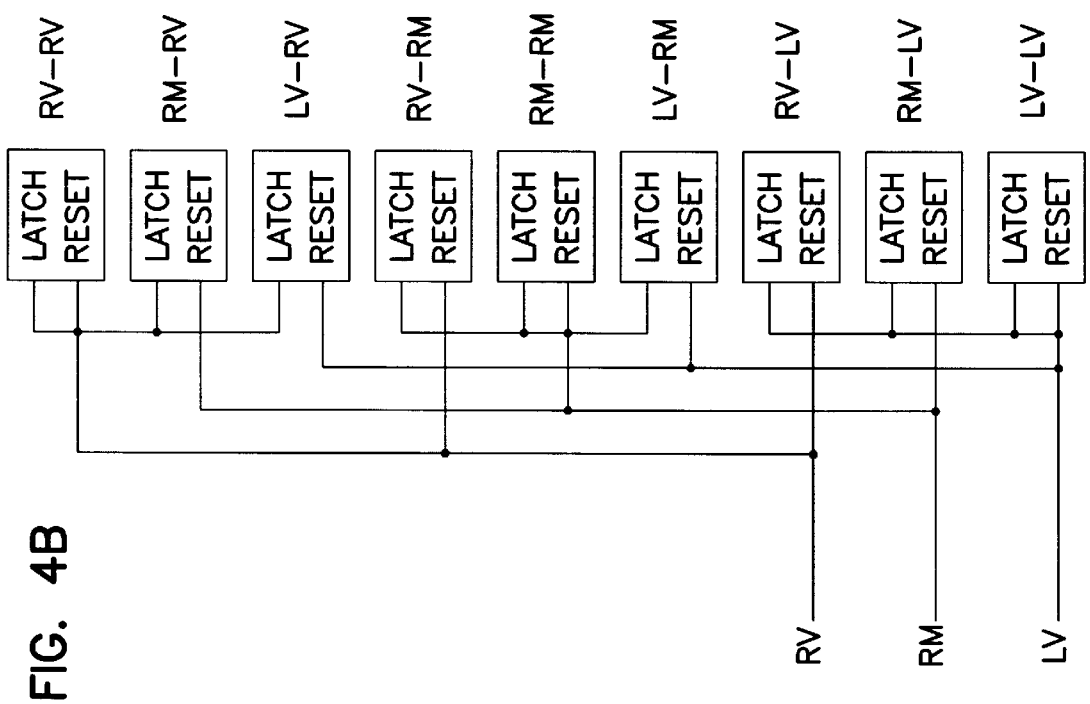
FIG. 4B is a schematic diagram illustrating generally one embodiment in which three electrode signals (e.g., RV, RM, LV) are used.

A first method to distinguish normal and abnormal beats detects depolarizations on a plurality of electrode signals for each beat. In one example of this method, an RV depolarization indicates that a beat has occurred. The time intervals between detection of the same depolarization at the various electrodes (RA, RV, LV, RM, LM) reflect the pattern and timing with which this depolarization propagates over the heart. FIG. 4B is a schematic diagram illustrating generally, by way of example, but not by way of limitation, one embodiment in which 3 electrode signals (e.g., RV, RM, LV) are used. The sensed depolarization on each electrode signal resets 3 interval timers (total of 9 timers) that measure time intervals initiated by the resetting event. The sensed depolarization on each electrode signal also latches the current value in 3 timers, each of which is reset by a different electrode signal, as illustrated in FIG. 4B. In this way, each time a depolarization passes over the heart, the set of 9 time intervals is obtained. These time intervals represent the pattern with which the depolarization reached different electrodes. Similarly, if 4 signals are used, then 16 intervals exist, and if 5 signals are used, then 25 intervals exist, etc. If the set of intervals for a particular beat fall outside of limits deemed normal, then that beat is classified as abnormal. In one embodiment, the abnormal limits vary with the heart rate. The abnormal limits may be programmed into the device as either population-based or patient-specific values.

A second method to distinguish normal beats from abnormal beats compares the morphology of one or more available signals (e.g., RV and/or RM and/or LM signals) with corresponding template morphologies for a normal beat. In one embodiment, an RV depolarization detection provides a triggering event. For each RV depolarization, a correlation coefficient between the selected morphology signal and a corresponding template morphology is computed. If the coefficient is smaller than a predetermined threshold value, then the current beat is classified as abnormal. In one embodiment, different template morphologies are used for different ranges of heart rates. Also, the threshold values may be programmed into the device using either population-based or patient-specific values.

A third method to distinguish normal and abnormal beats extracts features from one or more available signals and compares the extracted features with similar features for normal beats. Possible features include, by way of example, but not by way of limitation, QRS duration, R-wave amplitude, QT interval, and T-wave amplitude. For a particular beat, if the detected value of one or more features falls outside limits deemed normal, then the beat is classified as abnormal. In one embodiment, the normal limits vary with heart rate. Also, the normal limits may be programmed into the device either as population-based or patient-specific values.

In addition to these methods of classifying beats, other methods of identifying or classifying beats will also be suitable. Also, beat classification module 400 can also be used with lead configurations having a different number of electrodes or electrodes located in different locations. After beat classification module 400 classifies a detected heart beat, detection processing module 405 performs the processing required for trigger/marker detection.

In one embodiment, detection processing module 405 uses the beat-to-beat intervals and morphological data extracted from the signals by beat classification module 400 and also extracts any additional morphological measures required for trigger/marker detection. Detection processing module 405 is also capable of examining activity, respiration, and stroke volume signals received from one or more acceleration, acoustic and/or impedance sensors and provided by sensing module 320.

Device 105 includes a trigger/marker list 410, which lists the triggers/markers to be detected. List 410 includes members, for example, the types and natures of the particular trigger/marker sought to be detected. In one embodiment, each member of the list includes a corresponding predetermined comparison value. In one example, list 410 includes a member "long QRS duration" trigger/marker. For that member, list 410 also includes a comparison value indicating which QRS durations are long. In another example, list 410 includes a particular "short-long-short sequence" of intervals between beats classified as normal. For that member, list 410 also includes corresponding comparison values establishing the criteria for long and short intervals in the sequence. Alternatively, list 410 includes members that include one or more beats classified as abnormal.

In one embodiment, the type and nature of the triggers/markers in list 410 are obtained from research in the relevant clinical population. Several different types of triggers/markers exist. For example, a first basic type of triggers/markers, is referred to as "sequence type" triggers/markers. Sequence type triggers/markers are based on sequences of one or more beats. Examples of sequence type triggers/markers include, by way of example, but not by way of limitation, premature normal beats, premature abnormal beats, delayed normal beats, delayed abnormal beats, long-short intervals between beats, short-long intervals between beats, and multiple (couplets, triplets, etc) abnormal beats. Detection processing module 405 detects and counts the number of times each of the specified sequence type triggers/markers are present during a particular observation period.

An example of a second basic type of triggers/markers is referred to as "value type" triggers/markers. Value type triggers/markers are based on metrics from the available signals, which are compared to predetermined comparison values to determine whether the trigger/marker is present during a particular observation period. Examples of value type triggers/markers based on morphology intrinsic heart activity signals include, by way of example, but not by way of limitation, QRS duration, ST magnitude, QT interval, and R-wave amplitude. In one embodiment, detection of morphology-based value type triggers/markers is based only on consideration of one or more beats classified as normal. In one example, a trigger/marker is based on the most recent beat. In another example, the trigger/marker is based on an average of morphology values over some number of previous normal beats. In a further example, the trigger/marker is based on one or more abnormal beats. Other examples of value type triggers/markers are not based on the heart's electrical activity. Such value type triggers/markers include, by way of example, but not by way of limitation, present respiratory rate, a position in the respiratory cycle at which the beat is detected, tidal volume of a respiratory inhalation or exhalation, cardiac stroke volume, present activity level of the patient, or the current position within the diurnal cycle.

An example of a third basic type of triggers/markers is referred to as "history type" triggers/markers. In one embodiment, the presence or absence of history type triggers/markers is determined based on one or more possible computational analyses of historical data obtained from multiple beats or from multiple observation periods. Examples of history type triggers/markers include, by way of example, but not by way of limitation, a percentage of abnormal beats detected during an observation period, a percentage of premature or ectopic beats detected during an observation period, heart rate variability during an observation period (e.g., 5 minutes), and the presence of alternans (i.e., cyclic variations over a plurality of cardiac cycles, e.g., T-wave alternans or QRS alternans) during an observation period. Other examples of history type triggers/markers include, by way of example, but not by way of limitation, short-term and long-term averages of the beat-to-beat data, trends in such averages (e.g., increasing or decreasing ST elevation, increasing density of abnormal or premature beats, etc.), and trends or periodicities in sensor values obtained from sensing module 320.

In one embodiment, detection processing module 405 outputs a set of detection values, denoted $D_1, D_2, D_3, \ldots, D_N$, corresponding to the N members in list 410 and where each detection value, $D_i$, corresponds to a single member of list 410. In one embodiment, a detection value $D_i$ is set to 0 if the corresponding trigger/marker was not detected during the most recent observation period, and is set to 1 if the rigger/marker was detected during the most recent observation period.

Timing of Arrhythmia Predictions and Trigger/Marker Detection

Not all trigger/marker detections are updated on a beat-to-beat basis because some triggers/markers (e.g., history type triggers/markers) generally require information obtained from multiple beats. In one embodiment, the detection of riggers/markers is performed asynchronously from arrhythmia predictions. Several techniques can be used for this purpose. In one technique, each trigger/marker detection value corresponds to a predetermined observation period during which time its value (e.g., present, or not present) is determined. For many triggers/markers, the appropriate observation period is equal to a predetermined basic time period (BTP). For instance, if the basic time period is 2 minutes, then device 105 tests for the occurrence of such triggers/markers in the last 2 minutes. However, detection observation periods are not necessarily the same for each trigger/marker. In one embodiment, for example, a heart rate variability trigger/marker is based on an observation period of approximately 5 minutes.

Figure 5:
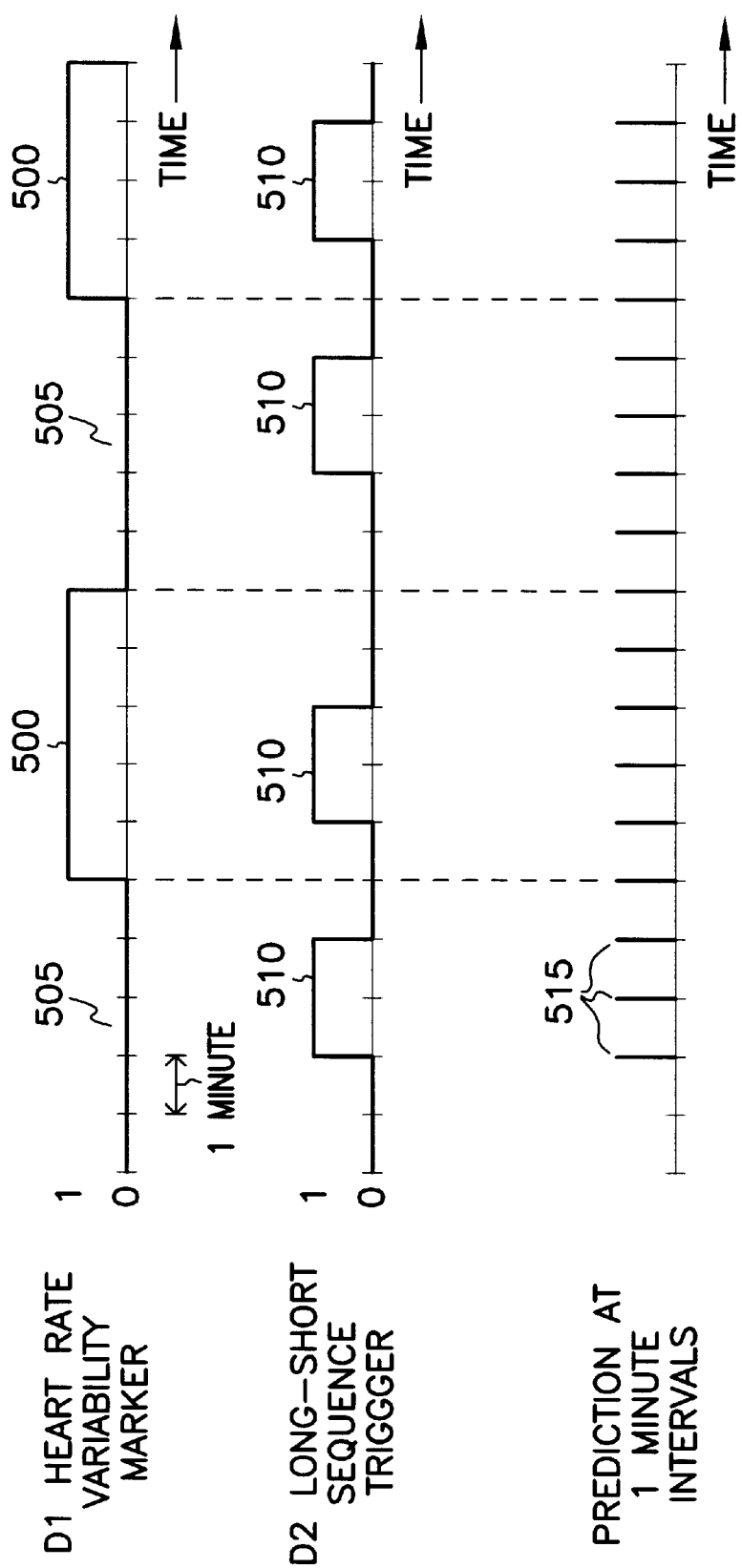
FIG. 5 is a timing diagram illustrating generally one embodiment of updating a heart rate variability marker.

FIG. 5 is a timing diagram illustrating generally, by way of example, but not by way of limitation, a heart rate variability trigger/marker, $D_1$, which is updated using a 5 minute observation period. In this example, $D_1=1$ during time periods 500 when heart rate variability is below its detection threshold and $D_1=0$ during other time periods 505 when heart rate variability is above its detection threshold. FIG. 5 also depicts a "long-short sequence" trigger, $D_2$, which is updated at 2 minute intervals. In this example, $D_2=1$ during time periods 510 when the long-short sequence has been detected in the preceding 2 minute observation period, and $D_2=0$ at other times. In this way, particular trigger/marker detection values are updated independently of other trigger/marker detection values in the set of trigger/marker detection values, D, as sufficient data for making the particular trigger/marker detection becomes available.

In one embodiment, predictions of future arrhythmias are made at approximately regular time intervals 415, such as at the BTP. In one embodiment, the BTP is based on a fixed number of beats (e.g., 60 beats). In another embodiment, the BTP is based on the number of beats closest to a fixed duration (e.g., the number of beats just exceeding 1 minute, such that the BTP remains approximately constant. In a further embodiment, the time duration of the BTP is adjusted over a period of time during which device 105 is being used, such that predictions of future arrhythmias are made more or less frequently at times when the predicted probability for arrhythmias is higher or lower, respectively.

Other Techniques for Timing Predictions of Arrhythmias

According to one aspect of the present arrhythmia prediction and prevention techniques, the prediction provides a good match between the time period covered by the prediction and the requisite times for one or more potential preventive therapies. For example, a prediction of a 99.9% chance that the patient will have an arrhythmia within the next 100 years is highly accurate but worthless because the prediction does not relate to when the prevention therapy should be delivered or which prevention therapy should be provided. Similarly, a prediction of a 50% chance that the patient will have an arrhythmia within the next 2 years is of limited value because it relates only to long-term prevention therapies such as selecting patients for device implant or for long-term drug or pacing therapy. By contrast, a prediction of a 50% chance that the patient will have an arrhythmia within the next 30 seconds provides great value in an arrhythmia prediction and prevention scheme in an implanted device provided that the decision to invoke a preventive therapy and the requisite time of action for that therapy can be carried out quickly enough to significantly reduce the chance of the future arrhythmia. In this example, the value of the prediction would be quite limited if the available preventive therapy required, for example, 20 minutes to take effect.

According to another aspect of the present arrhythmia prediction and prevention techniques, the prediction frequency adequately relates to the time period for which the prediction is valid. For example, it makes little sense for a prediction covering 1 month to be made once every 5 seconds or for a prediction covering 5 seconds to be made once every month. Thus, the present arrhythmia prediction and prevention techniques balance between the time period covered by a prediction, the frequency with which it is made, and the time required for the preventive therapy to take effect.

In one embodiment, device 105 does not necessarily make the same set of predictions each time predictions are made. One method to do so for the device to make one set predictions for each BTP that cover times on the order of the BTP. Then at BTP multiples that correspond to longer intervals (e.g. 20 minutes, 1 hour, 1 day, 1 week, 1 month), a corresponding sets of additional predictions are made which cover the correspondingly longer time intervals. The scheduling of the predictions, their corresponding time intervals are selected, according to the above argument, according to the times of action for the prevention therapies available to the device 105.

Arrhythmia Prediction Example

Figure 6:
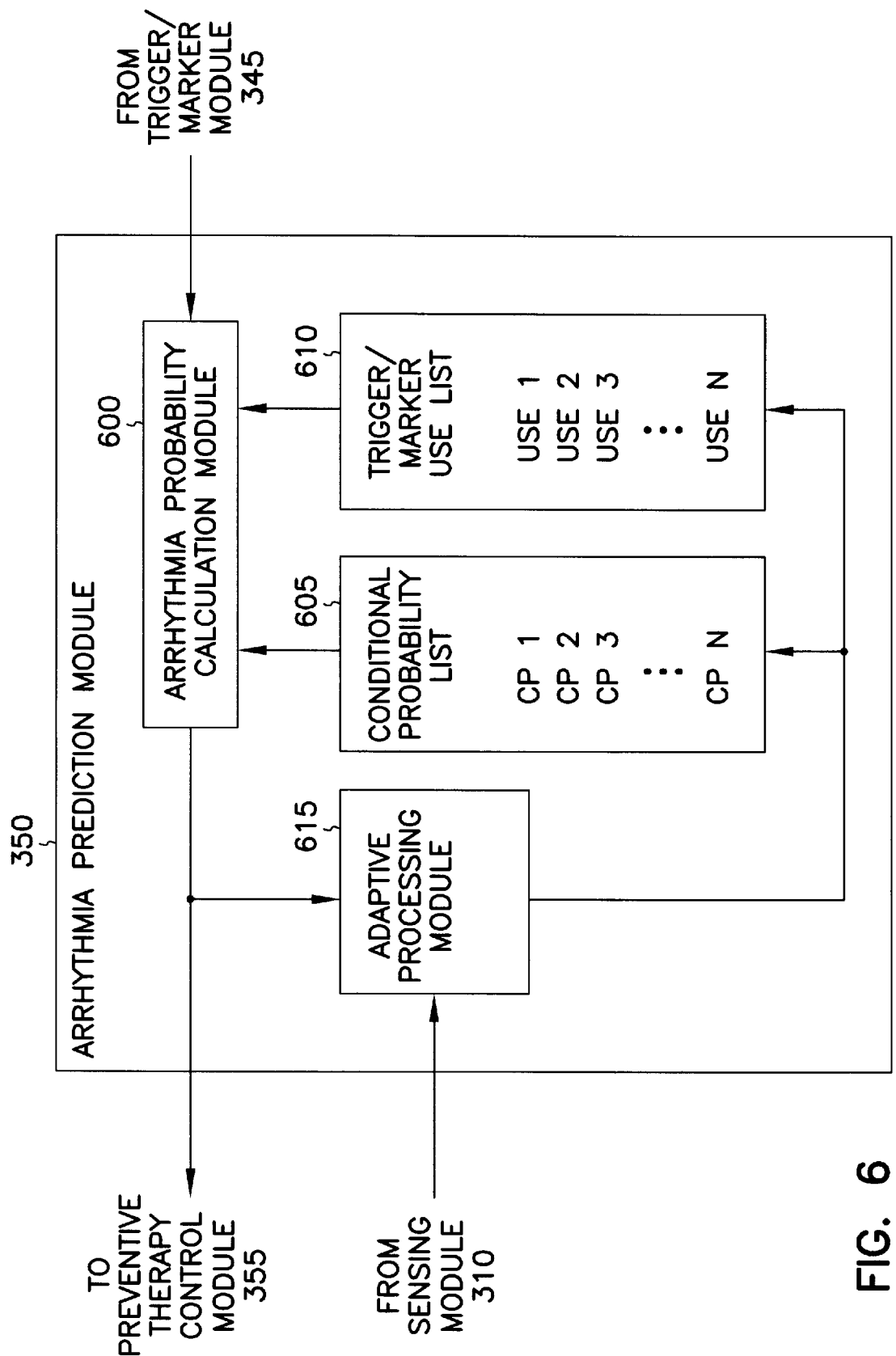
FIG. 6 is a block diagram illustrating generally one conceptual embodiment of portions of an arrhythmia prediction module.

FIG. 6 is a block diagram illustrating generally, by way of example, but not by way of limitation, one conceptual embodiment of portions of arrhythmia prediction module 350. In one embodiment, arrhythmia prediction module 350 includes an arrhythmia probability calculation module 600, a conditional probability data bank such as a list of conditional probabilities 605, trigger/marker use data bank such as trigger/marker use list 610. In a further embodiment, arrhythmia prediction module 350 also includes an adaptive processing module 615. In one embodiment, conditional probability list 605 and trigger/marker use list 610 each have members corresponding to the members of trigger/marker list 410, as explained below.

In one embodiment, arrhythmia prediction module 350 includes an input that receives the detection values ($D_1, \ldots D_N$) provided by trigger/marker module 345. In a further embodiment, arrhythmia prediction module 350 also includes input(s) that receive one or more "arrhythmia detected" signals provided by conventional arrhythmia detection modules of device 105 (e.g., signals from bradyarrhythmia control module 335 and tachyarrhythmia control module 340). These "arrhythmia detected" signals indicate, among other things, the presence or absence of one or more present bradyarrhythmias or tachyarrhythmias. Arrhythmia prediction module 350 outputs an arrhythmia prediction to preventive therapy control module 355, which, in turn, bases delivery of preventive therapy on the arrhythmia prediction.

One aspect of the present arrhythmia prediction techniques treats the occurrence of an arrhythmia during a particular time period as a random event. In this embodiment, an arrhythmia prediction includes a probability calculation estimating the probability that an arrhythmia will occur within a specified period after the prediction. An example of such a prediction is a 50% probability that an arrhythmia will occur within the next 2 minutes. This method of prediction includes both a degree (e.g., 50%) and a well defined time period during which the prediction is applicable (e.g., 2 minutes), as opposed to merely indicating that the patient is currently at risk.

In one embodiment, the arrhythmia prediction output from arrhythmia prediction module 350 includes a set of one or more arrhythmia probability assertions or statements. Each probability statement includes both a magnitude of the probability and a specified future time period associated therewith. In one embodiment, each probability statement also identifies which trigger, marker, or combination of trigger(s) and/or marker(s) contributed to its magnitude. In a further embodiment, the time period covered by each probability statement (i.e., the time period over which each probability statement is valid) is determined by, among other things, the scheduled prediction frequency (e.g., predictions made at 1 minute intervals cover a 1 minute period, etc.).

One conceptual approach to prediction recognizes that the rate at which arrhythmia events randomly occur changes relatively slowly compared to the time period over which predictions are made (i.e., the prediction frequency). Because future arrhythmia rates cannot be measured, predictions are based on one or more previous and/or present estimates of the arrhythmia rate assuming that the arrhythmia rate doesn't change significantly during the time period over which the prediction is made. The probability that a random arrhythmia event will occur within the specified prediction time period can be calculated based on the present arrhythmia rate. For simplicity, the occurrence of arrhythmia events can be understood as the result of a Poisson process with a rate, R. The probability, P, that one or more arrhythmias will occur within a next time period, T, is $P=(1-e^{-RT})$. The accuracy of P depends on the degree to which the estimate for R is correct, the rate R is truly constant during the time period T, and whether the underlying process is truly a Poisson random process. While such a conceptual approach may be helpful to understand the context of certain of the present prediction techniques, in one embodiment arrhythmia prediction module 305 does not actually formulate an estimate of the underlying arrhythmia rate. Instead, the arrhythmia rate is reflected in the presence or absence of the detected triggers/markers, which are used by arrhythmia probability calculation module 600 to formulate a probability for a future arrhythmia, as explained below.

For example, consider the Ith trigger/marker of trigger/marker list 410. In one embodiment, the detection value $D_I$ is either one or zero depending on the respective presence or absence of this trigger/marker during the basic time period equal to T. Further, consider that the rate of arrhythmias $R_I$ associated with this trigger/marker is zero when the trigger/marker is absent and that the rate $R_I$ has a nonzero value when the trigger/marker is present. The contribution of the Ith trigger/marker to the arrhythmia probability is $D_I(1-e^{-R_IT})$, or simply $D_I \times C_I$ where $CP_I$ is the conditional probability for the arrhythmia given that $D_I$ is present. The total probability for an arrhythmia, P, which includes the contributions from all trigger/markers, is computed as $P=D_1CP_1+D_2\times CP_2+D_3\times CP_3+ \ldots +D_N\times CP_N$, for the case where there is a detection value and a conditional probability for each member of the trigger/marker list 410.

In one embodiment, the conditional probabilities CP are obtained empirically from observations made in a patient population. In another embodiment, the conditional probabilities CP are seeded with population-based values, but are later adapted to the individual patient based on empirical observations of that patient. Because the conditional probabilities CP are empirically determined, the underlying process need not be exactly Poisson distributed, and the rate need not be completely unchanging during the time period T. The empirical estimations for the conditional probabilities CP incorporate deviations from these assumptions, although their predictive accuracy may be reduced. In one embodiment, a trigger/marker list 410 and a population-based conditional probability list 605 is loaded into device 105 before, during, or after device 105 is implanted in the patient.

In one embodiment, arrhythmia prediction module 350 also includes a trigger/marker use list 610, which provides a set of usage weights or flags, each usage weight or flag associated with a corresponding trigger/marker of trigger/marker list 410. According to one aspect of the present techniques, it may be desirable to exclude one or more of the trigger/marker detections from the total probability computation, such as, as the result of learning patient-specific traits by adaptive processing module 615. In trigger/marker use list 610, each usage weight or flag indicates how that trigger/marker detection value and conditional probability enters into the arrhythmia probability computation. In one embodiment, usage flags provide a binary indication of whether or not that particular trigger/marker detection value and conditional probability enters into the arrhythmia probability calculation. In another embodiment, usage weights provide a degree to which the detection value and conditional probability enters into the arrhythmia probability calculation. In such an embodiment, the arrhythmia probability calculation may be normalized, based on the values of the usage weights, such that the arrhythmia probability ranges between 0 and 1.

Determining Triggers/Markers and Conditional Probabilities from a Population

In one embodiment, a relevant patient population is used to obtain initial or actual estimates for conditional probabilities and/or to select particular triggers/markers for active use in the present prediction techniques. Patient-specific and adaptive techniques are described later. One approach for determining population-based parameters uses long-term data (e.g., from sensing module 310 and/or sensing module 320) from a representative subset of the clinically relevant population. This long-term data obtained from a plurality of patients in the clinically relevant patient population is referred to as the population database. Data in the population database is divided into time periods equal to the BTP. After each such time period, trigger/marker detection processing is performed over the entire population database for all triggers/markers. The presence or absence of each trigger/marker (i.e., the set of detection values, D) is noted after each such time period. The presence or absence of one or more arrhythmias is also noted after each such time period. One population-based estimate for a particular conditional probability associated with the Ith trigger/marker (i.e. $CP_I$) is simply $CP_I=$[(total number of time periods with arrhythmias that were preceded by a time period with $D_I$ present) ÷(total number of time periods with $D_I$ present)]. A similar estimate is made for all members in trigger/marker list 410. This embodiment uses time periods equal to the same duration (i.e., the BTP) for all triggers/markers. Alternatively, the population database is divided into equal-length time periods that are different between individual triggers/markers. For example, for each trigger/marker, the population database may be divided up into equal length time periods that correspond approximately to the time period covered by that particular trigger/marker.

Determining Predictive Capability of Particular Triggers/Markers

Not all possible triggers/markers may have predictive power, either in the clinically relevant patient population, or in the particular patient toward which the disclosed techniques are applied. The present techniques include a method of selecting those particular triggers/markers, in the trigger/marker list 410, that have useful predictive capability. One such method uses a Chi squared test based on the population database, but other statistical test methods may also be used. For example, in the Chi squared test, the presence or absence of arrhythmias and the available triggers/markers in each time period in the population database yields the following values: #BTP=total number of BTP's examined, #D$^+$=total number of BTP's in which the trigger/marker was detected, #D$^-$=total number of BTP's in which the trigger/marker was not detected, #A$^+$=total number of BTP's in which arrhythmia was detected, #A$^-$=total number of BTP's in which arrhythmia was not detected, # D$^+$A$^+$=number of BTP with the trigger/marker detected followed by a BTP with arrhythmia, # D$^+$A$^-$=number of BTP with the trigger/marker detected followed by a BTP without arrhythmia, # D$^-$A$^+$= number of BTP without the trigger/marker detected followed by BTP with arrhythmia, # D$^-$A$^-$=number of BTPs without the trigger/marker detected followed by BTP without arrhythmia.

A statistical test determines whether the observed occurrences of #D$^+$A$^+$, #D$^+$A$^-$, #D$^-$A$^+$, and #D$^-$A$^-$ are different from those that would be expected if the trigger/marker did not have predictive power. One example such test computes the following sum:

$$\text{Sum} = \left[\frac{\#D^+A^+ - \#A^+ \times \#D^+/\#BTP}{\#A^+ \times \#D^+ \div \#BTP}\right]^2 +$$
$$\left[\frac{\#D^+A^- - \#A^- \times \#D^+/\#BTP}{\#A^- \times \#D^+ \equiv \#BTP}\right]^2 +$$
$$\left[\frac{\#D^-A^+ - \#A^+ \times \#D^-/\#BTP}{\#A^+ \times \#D^-/\#BTP}\right]^2 +$$
$$\left[\frac{\#D^-A^- - \#A^- \times \#D^- \equiv \#BTP}{\#A^- \times \#D^- \equiv \#BTP}\right]^2$$

This represents the Chi Square value (1 degree of freedom) that tests if the arrhythmia is associated with the trigger/marker. If the sum exceeds 3.84, for example, we are 95% confident that the trigger/marker provides predictive capability for the arrhythmia. A more complete multi-variate statistical analysis would provide stronger conclusions about the trigger/marker's role when considered together with other triggers/markers having independent predictive power. Strictly speaking, the form for the above probability computation is based on an approximation, i.e., that the predictive capability of the individual triggers/markers are independent from each other.

Patient Specific Adaptive Processing Example

In one embodiment, device 105 includes a patient specific adaptive processing module 615, as illustrated in FIG. 6. In one example, adaptive processing module 615 modifies conditional probability list 605 and trigger/marker use list 610. The present techniques recognize that it is unlikely for some set of one or more triggers/markers to be so powerful at predicting arrhythmias that they always worked in all patients. The predictive capability of a particular set of one or more triggers/markers will most likely vary between different patients. Population-based average values may be suboptimal for a particular patient. In one embodiment, device 105 examines long-term data specific to the individual patient in which it is implanted. Thus, one aspect of the present techniques allow device 105 to adapt to an individual patient to improve the accuracy and confidence in arrhythmia predictions over a time during which device 105 is being used.

One embodiment extracts patient-specific parameters (e.g., conditional probabilities and/or weights) analogously to the techniques described above that extract population-based parameters. In this embodiment, the members of the trigger/marker list 410 are initially established based on clinical research in a population of interest, and are loaded into device 105. After implantation of device 105 in a particular patient, as ongoing data is acquired from the patient, adaptive processing module 615 manages trigger/marker use list 610 by determining which members of trigger/marker list 410 provide predictive capability for arrhythmia prediction in the particular patient.

One such technique initially sets the members of the trigger/marker use list 610 to "do not use." At some point after implant, adaptive processing module 615 examines each BTP to detect the presence or absence of (1) arrhythmias and (2) the triggers/markers in trigger/marker list 410 to form a patient-specific database. Device 105 recurrently performs the above Chi squared test to determine (to within a predetermined level of confidence) if each member of trigger/marker list 410 provides predictive capability in the particular patient. If a member does provide such predictive capability, the usage value for that member is set to "use" in trigger/marker use list 610. Such a technique only allows an arrhythmia prediction based on a particular trigger/marker after sufficient confidence exists that its predictive capability in the particular patient is sufficiently high.

Another such technique initially sets the members of the trigger/marker use list 610 to "use," such as where population based data indicates the likelihood that these members of the trigger/marker use list are likely to have sufficient predictive capability. In this embodiment, the corresponding usage values are set to "do not use" if the patient-specific database demonstrates that the trigger/marker does not provide adequate predictive capability in the particular patient despite its good performance in the population. Such a technique stops using the trigger/marker to make predictions after sufficient confidence exists that its predictive capability in the particular patient is inadequate.

For patient-specific adaptive processing, the ratios (R$^+_P$=# D$^+$A$^+$÷# D$^+$) and (R$^-_P$=# D$^-$A$^+$÷# D$^-$) from the population database (hence the P subscripts) are used to compute the following sum:

$$\text{Sum} = \left[\frac{\#D^+A^+ - R^+_P \times \#D^+}{R^+_P \times \#D^+}\right]^2 + \left[\frac{\#D^+A^- - (1-R^+_P) \times \#D^+}{(1-R^+_P) \cdot \#D^-}\right]^2 +$$
$$\left[\frac{\#D^-A^+ - R^-_P \times \#D^-}{R^-_P \times \#D^-}\right]^2 + \left[\frac{\#D^-A^- - (1-R^-_P) \times \#D^-}{(1-R^-_P) \times \#D^-}\right]^2$$

where the values of # D$^+$, # D$^+$A$^+$, etc. are obtained from the patient specific database. This sum, which is a Chi squared value, is compared to another predetermined threshold value. If the sum exceeds the threshold, then that trigger/marker does not predict the arrhythmia in the specific patient in the same manner as it does in the population. This could occur either if the trigger/marker provides lesser predictive power than in the population, or also if the trigger/marker provides greater predictive power than in the population. Consequently, the corresponding usage flag in trigger/marker use list 610 is only set to "do not use" if the patient-specific test also demonstrates that the trigger/marker does not provide predictive power in the particular patient. In one embodiment, these threshold values (population-based and/or patient-specific) are programmable. In a further embodiment, these threshold values (population-based or patient-specific) are programmed to either the same value, or to different values.

The predictive capability of a particular trigger/marker could change over time in a particular patient. In one embodiment, adaptive processing module 615 recurrently sets and/or resets the usage values in the trigger/marker use list 610 over time while device 105 is being used. In this embodiment, testing for patient-specific predictive capability of each trigger/marker is carried out recurrently. If a particular trigger/marker is not presently in use, then the test result (i.e., the sum described above) would be required to exceed a first threshold value to change the usage value of the trigger/marker to "use." If the trigger/marker is presently in use, then the test result (i.e., the sum described above) would be required to exceed a second threshold value to change the usage value of the trigger/marker to "do not use." These threshold values can either be the same, or alternatively can be different to provide hysteresis that would reduce the number of spurious transitions.

In one embodiment, adaptive processing module 615 also provides and adaptively modifies conditional probabilities in conditional probability list 605 based on observations in the specific patient. For a particular patient, a trigger/marker's conditional probability may vary from the population-based value. Conditional probability list 605 is initially seeded with population-based conditional probabilities. However, as device 105 acquires data from the particular patient, patient-specific conditional probabilities are used, as described below.

In one embodiment, adaptive processing module 615 implements the patient-specific conditional probabilities by recurrently estimating the conditional probability for each trigger/marker analogously to their population-based estimation described above. However, patient-specific data is used rather than population-based data. For each member of the trigger/marker list 410, device 105 estimates the patient-specific conditional probability as $CP_{I\ est} = \# D_I^+A^+ \div \# D_I^+$, where $\# D_I^+$ is number of BTP's in which the Ith trigger/marker was detected, and $\# D_I^+A^+$ is the number of BTP in which (1) trigger/marker I was detected, and (2) the BTP was followed by a BTP with an arrhythmia.

Such recurrent reforecasting of conditional probabilities also includes a second step of determining when the patient-specific values should be used rather than the population-based values. Counters storing $\# D_I^+A^+$ and $\# D_I^+$ are initially reset to zero. Whenever a BTP containing trigger/marker I is detected, device 105 formulates a new estimate for the conditional probability $CP_{I\ est}$ by incrementing $\# D_I^+$ and $\# D_I^+A^+$ if the following BTP includes an arrhythmia.

If the initial value for $CP_I$ is also correct for the particular patient, then after observing $\# D_I^+$ BTP's with trigger/marker I, one would expect ($\# D_I^+ \times CP_I$) cases where an arrhythmia was found. More or fewer arrhythmias may result from chance alone. The standard deviation for the number of expected arrhythmias is $\{\# D_I^+ \times CP_I (1-CP_I)\}^{1/2}$. A 95% confidence interval would include about 1.96 times this standard deviation above and below the expected values. Thus, if the initially entered values for $CP_I$ were also valid for this particular patient, then there exists a 95% confidence that the number of arrhythmias observed after $\# D_I^+$ occurrences of trigger/marker I is between $[\# D_I^+ \times CP_I - 1.96 \{\# D_I^+ \times CP_I \times (1-CP_I)\}^{1/2}]$ and $[\# D_I^+ \times CP_I + 1.96 \{\# D_I^+ \times CP_I \times (1-CP_I)\}^{1/2}]$. Expressed as percentages of $\# D_I^+$, this yields the following confidence interval for the conditional probability: $[CP_I - 1.96 \times \{CP_I \times (1-CP_I)/\# D_I^+\}^{1/2}]$ and $[CP_I + 1.96 \times \{CP_I \times (1-CP_I)/\# D_I^+\}^{1/2}]$.

If the estimate for the conditional probability $CP_{I\ est}$ falls outside this range, there exists a 95% confidence that $CP_{I\ est}$ is a better estimate for this particular patient than $CP_I$. In that case, the estimated value for the conditional probability is used for subsequent predictions of future arrhythmias rather than the population-based values. Because the patient's conditional probabilities may change over time, the same procedure can be repeated recurrently by using the new conditional probability as the given value and forming another new estimate based on a new set of observations. In this way, the conditional probabilities are recurrently updated to more appropriate values as device 105 is being used.

One alternate method of updating conditional probabilities recurrently updates the patient-specific conditional probability for each trigger/marker in such a way that the values eventually approach or track the true values for the specific patient. In this method, the conditional probabilities are seeded with population-based values. Then, each time a BTP containing one of the triggers/markers is observed, device 105 notes the presence or absence of an arrhythmia during the next BTP. If an arrhythmia is present, then the conditional probability for that trigger/marker is increased by a small step (e.g., $CP_I = CP_I + STEP^*(1-CP_I)$). If the arrhythmia is not present, then the conditional probability for that trigger/marker is decreased by a small step, as illustrated below (e.g., $CP_I = CP_I - STEP^*(CP_I)$).

If the patient's true conditional probability equals $CP_I$, then the ratio of BTP's with arrhythmias absent to those with arrhythmias present should equal $(1-CP_I)/CP_I$. For a conditional probability of 20%, for example, an average of 4 BTPs without arrhythmias are expected for each BTP with an arrhythmia. In this case, the conditional probability is decreased 4 times by a small amount (0.2×STEP) but increased 1 time by a large amount (0.8×STEP), yielding no net drift in the $CP_I$ over time. If the patient's actual conditional probability was significantly higher than $CP_I$, then there would be a higher proportion of BTP's with an arrhythmia. As a result, $CP_I$ would tend to increase until $CP_I$ approached the correct value. Similarly, if the actual value was too low, $CP_I$ would decrease until it approached the correct value. In one embodiment, the selection of STEP is small (~0.05) such that these changes are stable over time.

Examples of Alternate Methods for Arrhythmia Prediction

In one alternate embodiment, arrhythmia prediction module 350 incorporates into an arrhythmia prediction the number of times a trigger/marker occurs during a BTP or other time period. An arrhythmia may occur each time a particular trigger/marker occurs. Repeated appearances of a trigger/marker may suggest a stronger relative predictive value. Consequently, multiple occurrences of a trigger/marker provide a higher arrhythmia probability. In this embodiment, each member in the conditional probability list 605 includes a set of one or more conditional probability values. In one example, the first value in the set reflects the conditional probability when the corresponding trigger/marker occurred once during the basic time period, the second set reflects the conditional probability when the corresponding trigger/marker occurred twice during the basic time period, etc. In this embodiment, the set of conditional probabilities may alternatively reflect ranges of the number of trigger/marker detections (e.g., between 3 and 5 detections, fewer that 8 detections, more than 3 detections, etc.). The population-based and patient-specific values for these sets of conditional probabilities are also obtained by extension of the techniques described above. The patient-specific adaptive processing for these sets of conditional probabilities is also obtained by extension of the techniques described above.

This alternate embodiment also provides a different technique of trigger/marker detection. Instead of setting the detection value, $D_I$, to either zero or one, the trigger/marker detection processing module 405 sets the detection value $D_I$ to the number of times the Ith trigger/marker occurred during the BTP. The arrhythmia probability calculation is computed as $P=D_1\times P_{1,D1}+D_2\times CP_{2,D2}+D_3\times CP_{3,D3}+\ldots+D_N\times CP_{N,DN}$, where $CP_{I,K}$ is the conditional probability when trigger/marker I is present K times during the BTP, and N is the number of triggers/markers.

A second alternate embodiment recognizes that if two (or more) different triggers/markers occur during the same BTP, the probability for arrhythmias may be different from the linear sum of the conditional probabilities when the trigger/marker occurred alone (i.e., without the other one or more triggers/markers). In this embodiment, detection processing module 405 outputs binary detection values for the members in the trigger/marker list 410. However, in this embodiment, arrhythmia prediction module 350 forms a number from 0 (none of triggers/markers in trigger/marker list 410 detected) to $2^N-1$ (all of the triggers/markers in trigger/marker list 410 detected) indicating which of the triggers/markers in trigger/marker list 410 were detected during the BTP, where N is the number of members in trigger/marker list 410. In this embodiment, the members of conditional probability list 605 and trigger/marker use list 610 do not correspond to the members of trigger/marker list 410. Instead, the members of conditional probability list 605 and trigger/marker use list 610 correspond to the various combinations of the $2^N-1$ possible combinations of triggers/markers that could be detected. The arrhythmia probability calculation is computed as $P=CP_K$, where K is a number (from 0 to $2^N-1$) that reflects the current combination of detected triggers/markers (i.e., those triggers/markers having a detection value of 1).

Automated Preventive Therapy Selection Processing Example

Preventive therapy control module 355 automatically decides whether to invoke preventive therapy based on arrhythmia probability statements obtained from arrhythmia prediction module 350. Preventive therapy control module 355 provides output signals to therapy module 315 to deliver pacing and/or shock and/or other arrhythmia prevention therapies.

Figure 7:
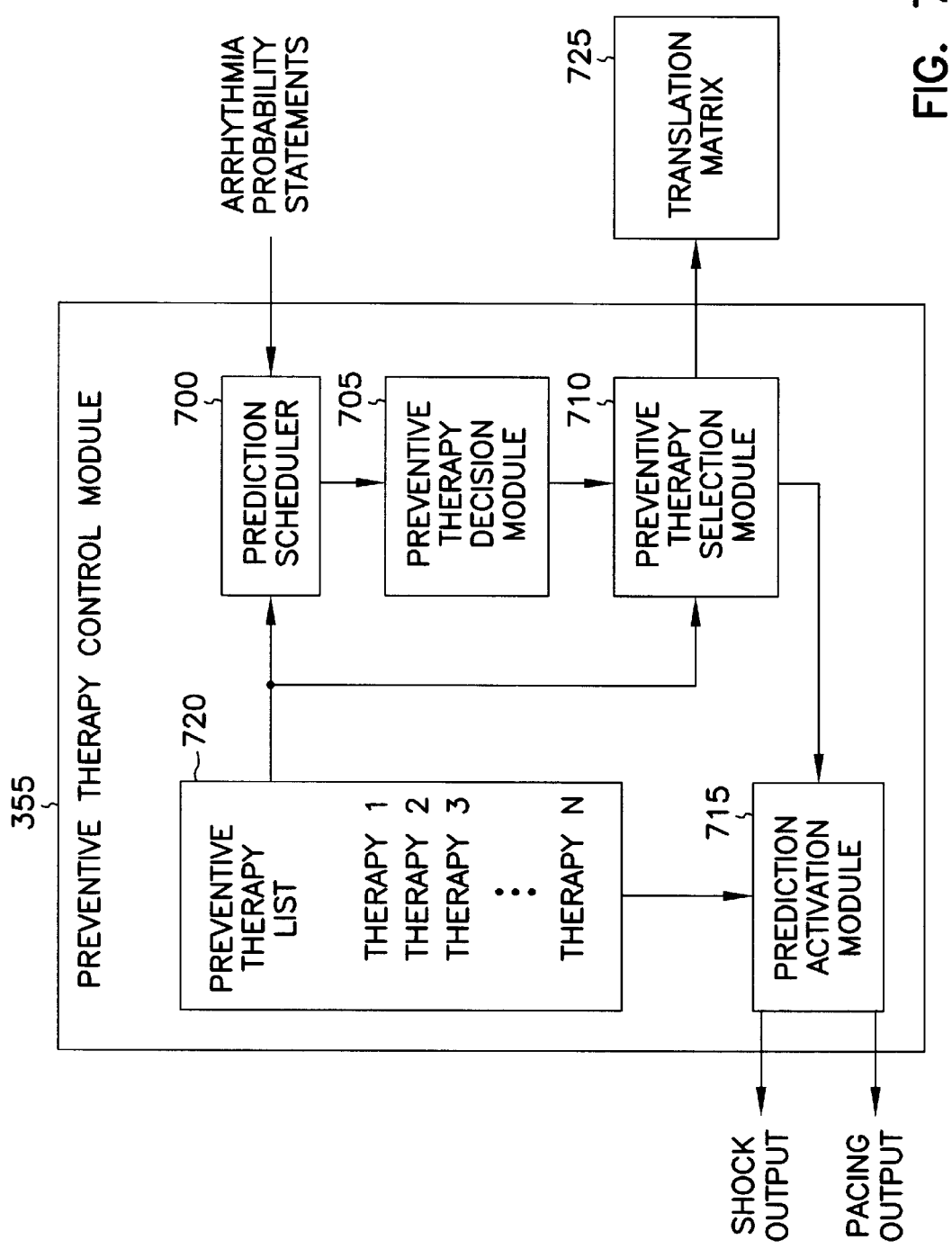
FIG. 7 is a block diagram illustrating generally one conceptual embodiment of portions of a preventive therapy control module.

FIG. 7 is a block diagram illustrating generally, by way of example, but not by way of limitation, one conceptual embodiment of portions of preventive therapy control module 355. In this embodiment, prediction scheduler 700 schedules predictions of future arrhythmias. Preventive therapy decision module 705 decides whether arrhythmia prevention therapy is warranted. Preventive therapy selection module 710 selects one or more appropriate prevention therapies. Prevention activation module 715 activates the selected arrhythmia prevention therapy. Preventive therapy control module 355 also includes a prevention therapy list 720, and a trigger/marker vs. preventive therapy translation matrix 725 that relates the prevention therapies of preventive therapy list 720 to the triggers/markers used by arrhythmia prediction module 350 in predicting future arrhythmias. The various submodules in therapy control module 355 are illustrated as such for conceptual purposes only; alternatively, these submodules may be understood as being incorporated in arrhythmia prediction module 350 or elsewhere.

In one embodiment, prevention therapy list 720 includes all the possible arrhythmia prevention therapies that device 105 can deliver to the patient. List 720 is programmed into device 105 either in hardware, firmware, or software. The members of list 720 may be selected based, by way of example, but not by way of limitation on: the patient's lead and electrode configuration, the patient's dependence on pacing, functionality of the patient's AV node, etc. In one embodiment, each member of preventive therapy list 720 includes information fields (e.g., pacing rate, interval sequences, etc.) that establish characteristics of that particular arrhythmia prevention therapy. In one embodiment, preventive therapy list 720 includes immediate, short-term, intermediate-term, and/or long term preventive therapies.

Immediate preventive therapies include, by way of example, but not by way of limitation: overdrive atrial pacing, such as for patients with functional AV nodes; demand atrial pacing, such as for patients with functional AV nodes; overdrive ventricular pacing; demand ventricular pacing; simultaneous or sequenced overdrive atrial and ventricular pacing; simultaneous or sequenced demand right ventricular and left ventricular overdrive pacing, such as for patients with a left ventricular pacing electrode; simultaneous or sequential right ventricular and left ventricular demand pacing, such as for patients with a left ventricular pacing electrode.

Short-term preventive therapies include, by way of example, but not by way of limitation: repetitive overdrive atrial pacing, such as for patients with functional AV nodes; repetitive simultaneous or sequenced demand atrial and ventricular pacing; subthreshold cardiac stimulation, such as using defibrillation lead electrodes; neural stimulation of the autonomic nervous system, such as for patients with autonomic stimulation leads; global pacing pulses implemented by providing low energy shocks via defibrillation electrodes; delivery of certain drugs.

Intermediate-term preventive therapies include, by way of example, but not by way of limitation, an alert/warning for the patient and/or physician such as by providing an audible tone or other signal; delivery of certain drugs.

Long-term preventive therapies include, by way of example, but not by way of limitation, diagnostic warnings for the physician, such as by transmitting diagnostic information from device 105 to external programmer 125 using a telemetry or other communication link; delivery of certain drugs.

According to one aspect of the present system, each member of preventive therapy list 720 is associated with a required time of action, which includes one or more of a time for the therapy to become effective and/or a time after which the therapy is no longer effective. Accordingly, in one embodiment, the prediction scheduler 700 considers only those members of the preventive therapy list that can be expected to be effective within a time frame commensurate with the prediction time period. In other embodiments, information relating to the time frame in which a particular therapy is expected to be effective is incorporated into the translation matrix 725, and the prediction time period is added to the trigger/marker list 410. Other physiological variables can also be added to the list 410 to form a kind of physiological state vector that can be mapped to a particular member of the preventive therapy list 720, with the translation matrix incorporating information relating to the appropriateness each member of the therapy list for a given value of a physiological variable.

In one embodiment, only one member of the preventive therapy list 720 is invoked at any particular time. Combinations of different preventive therapies are also provided, but each such combination is treated as a separate entry in preventive therapy list 720. For example, "initiate overdrive ventricular pacing" is one member in preventive therapy list 720 while "initiate an alert/warning stimulus" is a different member in preventive therapy list 720. A combined therapy using both "initiate overdrive ventricular pacing" and "initiate an alert/warning stimulus" is treated as yet another entry in preventive therapy list 720. This simplifies the tasks of preventive therapy selection module 710 and prevention activation module 715.

Preventive therapy selection module 710 selects an arrhythmia prevention therapy based on outputs from preventive therapy decision module 705. If preventive therapy decision module 705 determines that the degree and confidence in the arrhythmia prediction warrant some preventive therapy, as discussed above, then preventive therapy selection module 710 selects a member of the preventive therapy list 720 to be invoked. In one embodiment, the selection of a prevention therapy is based on the set of trigger/marker detection values, D, upon which preventive therapy decision module 705 based the decision to provide arrhythmia prevention therapy. Translation matrix 725 translates between the trigger/marker detection values D and selection of the appropriate arrhythmia prevention therapy from preventive therapy list 720.

FIG. 8 is a diagram illustrating generally, by way of example, but not by way of limitation, one embodiment of a translation matrix 725. In this embodiment, rows of translation matrix 725 correspond to the members of trigger/marker list 410. Columns of translation matrix 725 correspond to the members of preventive therapy list 720. In one embodiment, the cells in translation matrix 725 are set to either "Use," "Do Not Use," or "Don't Care." A "Use" entry indicates that the corresponding preventive therapy is expected to provide a beneficial effect to reduce the risk of the arrhythmia when the associated trigger/marker is present. A "Do Not Use" entry indicates that the corresponding preventive therapy is expected to result in a detrimental effect that may increase the risk of arrhythmia when the associated trigger/marker is present. The "Don't Care," entry indicates that the corresponding preventive therapy is expected to neither increase or decrease the risk of arrhythmia when the associated trigger/marker is present.

For the particular example illustrated in FIG. 8, when the first member of trigger/marker list 410 is present, preventive therapies #1 and #6 are likely to be useful, but preventive therapy #4 should not be used because it is likely to be detrimental. The other possible preventive therapies are deemed to have no effect when trigger/marker #1 is present.

In one embodiment, the values in translation matrix 725 are population-based values that are initially loaded into device 105. These population-based values are obtained for the population of interest based on observations of: the occurrences of arrhythmias; the presence of preceding triggers/markers; and the estimated or empirically derived effect of the particular preventive therapies on decreasing the probability of arrhythmia.

In one embodiment, when preventive therapy decision module 705 indicates that a preventive therapy is needed, there will be some set of detected triggers/markers that initiated the decision to invoke arrhythmia prevention therapy. Therapy selection module 710 considers those rows in translation matrix 725 that correspond to those particular triggers/markers that initiated arrhythmia prevention therapy. Selection of the appropriate preventive therapy is based on a score determined for each of the preventive therapies in preventive therapy list 720. The particular preventive therapy with the highest score is selected by preventive therapy selection module 710.

In one embodiment, each member of preventive therapy list 720 is considered. For those rows that correspond to the presently detected triggers/markers, the number of "Use" entries is added to obtain the score. If any "Do Not Use" entry is present, however, the score is set to zero. In this way, each of the preventive therapies has a score between zero and the number of detected triggers/markers having a corresponding "Use" entry. Therapy selection module 710 selects that preventive therapy with the highest score. Where there is a tie, the preventive therapy appearing earliest in preventive therapy list 720 is used. Where all possible preventive therapies have a score of zero, then none of the available preventive therapies are deemed appropriate, and no preventive therapy is invoked. In one alternate embodiment, the score is also based on the conditional probability for each detected trigger/marker. In another alternate embodiment, a threshold value is included, such that the highest scoring preventive therapy must have a score that reaches (or exceeds) the threshold value before any preventive therapy is selected.

Prevention activation module 715 uses the information contained in the preventive therapy list 720 and/or translation matrix 725 for activating delivery of the selected therapy by therapy module 315. Device 105 delivers the activated therapy for a predetermined amount of time, which is also included in the preventive therapy list 720. The arrhythmia prevention therapy is delivered, by way of example, but not by way of limitation, by controlling the pacing and/or shock circuits or by storing information for later review (via telemetry or other communication to external programmer 125) by the physician or other user.

Example of Scheduling Predictions

Prediction scheduler 700 schedules the frequency with which arrhythmia predictions are made. As discussed earlier, the BTP used to detect a trigger/marker for prediction may differ from the time period covered by a particular prediction which, in turn, may differ from the time required for the preventive therapy to have an effect. Prediction scheduler 700 should schedule predictions in a rational manner, for allowing efficient operation.

As described above, the arrhythmia probability statements can be conceptualized as having the following basic form: "In the next Y time period there is an X percent chance of arrhythmia due to the combination of triggers/markers D." In one embodiment, predictions are made at a maximum of 2 minute intervals, and the BTP for detecting triggers/markers is also 2 minutes. In an alternate embodiment, however, the prediction frequency may be different from the BTP frequency. Intervals between predictions may be longer or shorter than the BTP, and may be variable or fixed. In one embodiment, the time period covered by the predictions (i.e., the values for Y) are either 2 minutes (i.e., 1 BTP), 30 minutes (i.e., 15 BTPs), 1 day, 1 week, or 1 month. Predictions covering a 2 minute period are made at 2 minute intervals. Predictions covering a 30 minute period are made at 10 minute intervals. Predictions covering a 1 day period are made at 6 hour intervals. Predictions covering a 1 week period are made daily. Predictions covering a 1 month period are made weekly. Thus, in this embodiment, the predictions covering shorter time periods are made at a frequency corresponding to the time period covered by the prediction. Predictions covering longer time periods are made more often than the time period covered by the prediction. The timing of the predictions relative to the time covered by the prediction could be made in many other ways without departing from the techniques disclosed in this document.

Preventive Therapy Decision

Preventive therapy decision module 705 decides whether preventive therapy is warranted. In one embodiment, this task is performed at each 2 minute interval (i.e., every BTP), at which time it considers all arrhythmia predictions existing at that time. In one embodiment, the total probability for arrhythmia for each of the prediction time periods is compared to corresponding threshold values.

If the arrhythmia probabilities during all of covered time periods fail to exceed the corresponding threshold values, then no significant arrhythmia risk is deemed to exist and no preventive therapy is provided. If the arrhythmia probability during any of the covered time periods exceed the corresponding threshold value, then a significant arrhythmia risk is deemed to exist, and the arrhythmia prevention therapy is selected and activated as described above.

Conclusion

Although the above description described particular embodiments using an implanted cardiac rhythm management device including defibrillation capability, the techniques can also be used in other cardiac rhythm management systems including, without limitation, implanted or external pacemakers, or other acute or chronic cardiac care or monitoring devices. Moreover, although the techniques were described using those electrodes and sensors available in implanted cardiac rhythm management devices, different and/or additional sensing and/or stimulation electrodes may be used (e.g., for sensing or stimulating sympathetic or parasympathetic nerves or ganglion, or for sensing pH, $pO_2$ or K+ concentration in blood, etc.).

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method, comprising:
   detecting a conditioning event statistically associated with the occurrence of an arrhythmia in a patient's heart; and,
   predicting the occurrence of an arrhythmia within a specified prediction time period if an estimated arrhythmia probability exceeds a specified threshold value, wherein the estimated arrhythmia probability is computed from a conditional arrhythmia probability associated with the conditioning event that is derived from past observations of instances in which the conditioning event occurs alone or together with an arrhythmia within a specified time period.

2. The method of claim 1 wherein the conditioning event is a marker event corresponding to detection of a physiological state statistically associated with occurrence of cardiac arrythmias.

3. The method of claim 1 wherein the conditioning event is a trigger event that increases the risk of an arrhythmia occurring via a depolarization that serves as a source for the arrhythmia.

4. The method of claim 1 wherein the conditioning event is a specific morphology of a waveform representing electrical activity of the heart.

5. The method of claim 1 wherein the conditioning event is a specific pattern of activation times of different areas of the heart as sensed by a plurality of electrodes.

6. The method of claim 1 wherein the conditioning event is a specific sequence pattern of heartbeats with respect to time.

7. The method of claim 1 wherein the conditioning event is a value of a measured physiological variable.

8. The method of claim 1 wherein the conditioning event is a statistic based upon a history of occurrences of conditioning events.

9. The method of claim 1 wherein the conditional arrhythmia probability CP is a ratio of the number of observed instances in which the conditioning event is followed by an arrhythmia within a specified basic time period to the total number of observed instances of the conditioning event.

10. The method of claim 9 further comprising estimating a rate C at which the conditioning event occurs, and further wherein the estimated arrhythmia probability is calculated by the expression:

$$\text{estimated arrhythmia probability} = CP \times (1 - e^{-CT}).$$

11. The method of claim 1 wherein the conditional arrhythmia probability is calculated by the expression:

$$1 - e^{-RT}$$

where T is a measure of the specified prediction time period, and R is an estimate of the rate at which arrhythmias occur while the conditioning event is present.

12. The method of claim 11 wherein the rate R is a ratio of: 1) the number of instances in which the conditioning event is followed by an arrhythmia within a specified basic time period, to 2) the length of the basic time period multiplied by the total number of basic time periods in which the conditioning event is observed.

13. The method of claim 12 further comprising estimating a rate C at which the conditioning event occurs, and further wherein the estimated arrhythmia probability is calculated by the expression:

$$(1 - e^{-RT})(1 - e^{-CT}).$$

14. The method of claim 1 further comprising assigning a culpability to a conditioning event for causing an observed instance of an arrhythmia when a specified criterion is met, and further wherein the conditional arrhythmia probability CP is a ratio of the number of observed instances in which the conditioning event was deemed culpable for causing an arrhythmia, to the total number of observed occurrences of the conditioning event.

15. The method of claim 14 further comprising estimating a rate C at which the conditioning event occurs, and further wherein the estimated arrhythmia probability is calculated by the expression:

$$\text{estimated arrhythmia probability} = CP \times (1 - e^{-CT}).$$

16. The method of claim 14 wherein the culpability criterion is the proximity in time between the conditioning event and the onset of an arrhythmia.

17. The method of claim 14 wherein the culpability criterion is the magnitude of the detected conditioning event prior to the onset of an arrhythmia.

18. The method of claim 14 wherein the culpability criterion is the frequency of occurrence of the conditioning event within a specific time period prior to the onset of an arrhythmia.

19. The method of claim 1 wherein a plurality of conditioning events statistically associated with the occurrence of an arrhythmia are detected and further wherein a composite estimated arrhythmia probability is compared with the threshold value in order to predict the occurrence of an arrhythmia, the composite arrhythmia probability being a combination of the estimated arrhythmia probabilities associated with each detected conditioning event.

20. The method of claim 19 wherein the composite arrhythmia probability is calculated by adding the estimated arrhythmia probabilities associated with each detected conditioning event.

21. The method of claim 20 wherein the estimated arrhythmia probabilities associated with each detected conditioning event are calculated by multiplying the conditional arrhythmia probability derived for a conditioning event by the number of detected occurrences of the event within a specified time period.

22. The method of claim 19 wherein each conditional arrhythmia probability is a ratio of the number of instances in which the conditioning event is observed to be followed by an arrhythmia within a specified basic time period to the total number of observed instances of the conditioning event.

23. The method of claim 22 wherein the conditional arrhythmia probabilities are derived using different basic time periods.

24. The method of claim 19 wherein the conditional arrhythmia probabilities are based upon past observations of the occurrences of events and arrhythmias taken from population data.

25. The method of claim 19 wherein the conditional arrhythmia probabilities are based upon past observations of the occurrences of events and arrhythmias taken in real-time from a particular patient.

26. The method of claim 25 wherein the conditional arrhythmia probabilities are based initially upon past observations of the occurrences of events and arrhythmias taken from population data and each probability is subsequently updated from a previous value to a present value with observations taken in real-time from a particular patient.

27. The method of claim 25 further comprising periodically updating a conditional arrhythmia probability from a previous value to a present value with observations taken in real-time from a particular patient.

28. The method of claim 27 wherein a conditional arrhythmia probability is updated only if the present value differs by a predetermined amount from the previous value.

29. The method of claim 28 further comprising testing the amount by which the present value differs from the previous value for statistical significance before a conditional arrhythmia probability is updated.

30. The method of claim 25 further comprising testing the statistical association of a conditional arrhythmia probability with real-time observation data.

31. The method of claim 30 further comprising discontinuing use of a conditional arrhythmia probability in deriving a composite conditional probability if the statistical association is below a specified value.

32. The method of claim 25 further comprising incrementing or decrementing a conditional arrhythmia probability by a specific amount after a prediction time period in accordance with whether the arrhythmia occurred or not, respectively.

33. The method of claim 19 wherein a separate estimated arrhythmia probability is computed for each of a plurality of types of arrhythmias.

34. The method of claim 1 further comprising delivering a preventive arrhythmia therapy if the estimated arrhythmia probability exceeds a exceeds a therapy threshold.

35. The method of claim 34 further comprising selecting a particular therapy to be delivered from a group of one or more available therapy modalities.

36. The method of claim 35 wherein the group of available therapy modalities includes delivery of one or more of a plurality of pharmacological agents.

37. The method of claim 35 wherein the group of available therapy modalities includes modalities selected from a group consisting of cardiac pacing in a selected pacing mode, delivery of cardioversion/defibrillation shocks, and neural stimulation.

38. The method of claim 35 wherein the group of available therapy modalities includes issuance of a warning signal.

39. The method of claim 35 wherein the selection of a particular therapy to be delivered is based upon ascertaining a physiologic state of the patient and deciding whether or not a particular available modality of therapy is appropriate for delivery to the patient in that physiologic state.

40. The method of claim 39 wherein the physiologic state ascertained for selecting a therapy modality includes the prediction time period of the estimated arrhythmia probability.

41. The method of claim 39 wherein the physiologic state ascertained for selecting a therapy mode includes the particular conditioning events used to make the arrhythmia prediction.

42. The method of claim 39 wherein the physiologic state ascertained for selecting a therapy mode includes the presence or not of specific conditioning events within a specified prior time period.

43. The method of claim 39 wherein the physiologic state ascertained for selecting a therapy mode includes the magnitude of a measured physiologic variable.

44. The method of claim 39 wherein the decision as to whether or not to deliver a particular mode of preventive therapy takes the form of a matrix mapping of a state vector representing a specific physiologic state to a specific therapy or therapies considered most appropriate for preventing an arrhythmia in that physiologic state, wherein the matrix mapping is performed using a translation matrix containing information relating to the appropriateness of a particular therapy modality for a given physiologic state.

* * * * *

UNITED STATES PATENT AND TRADEMARK OFFICE
CERTIFICATE OF CORRECTION

PATENT NO. : 6,272,377 B1
DATED : August 7, 2001
INVENTOR(S) : Robert J. Sweeney, Bruce H. KenKnight It is certified that error appears in the above-identified patent and that said Letters Patent is hereby corrected as shown below:

Column 15,
Lines 44-45, delete "$D_f(1-e^-_{RT})$" and insert -- $D_f(1-e^{-RT})$ --, therefor.

Signed and Sealed this

Nineteenth Day of March, 2002

Attest:

JAMES E. ROGAN
Attesting Officer     Director of the United States Patent and Trademark Office